United States Patent [19]

Mewman, Jr. et al.

[11] Patent Number: 5,028,694

[45] Date of Patent: Jul. 2, 1991

[54] **ANTIGENIC PROTEINS AND VACCINES CONTAINING THEM FOR PREVENTION OF COCCIDIOSIS CAUSED BY EIMERIA *EIMERIA NECATRIX* AND *EIMERIA TENELLA***

[75] Inventors: Karel Z. Mewman, Jr.; John L. Tedesco; Thomas C. Gore; Gary R. Petersen, all of Charles City, Iowa; Virginia M. Brothers, Albany, Calif.; James G. Files, Belmont, Calif.; Leland S. Paul, Woodside, Calif.

[73] Assignee: Solvay & Cie, S.A., Brussels, Belgium

[21] Appl. No.: 805,301

[22] Filed: Dec. 3, 1985

[51] Int. Cl.$^5$ .............................................. C07K 15/04
[52] U.S. Cl. .................................... 530/350; 424/88; 424/93; 530/806; 530/825
[58] Field of Search ...................... 424/88, 93; 530/350

[56] References Cited

U.S. PATENT DOCUMENTS

| | | | |
|---|---|---|---|
| 4,189,537 | 2/1980 | Martin et al. | 435/75 |
| 4,438,097 | 3/1984 | Shirley | 424/88 |
| 4,710,377 | 12/1987 | Schenkel et al. | 424/88 |
| 4,874,705 | 10/1989 | Andrews et al. | 435/252.33 |

*Primary Examiner*—Margaret Moskowitz
*Assistant Examiner*—Keith C. Furman
*Attorney, Agent, or Firm*—John P. White

[57] ABSTRACT

A purified antigenic protein has been obtained which is capable of inducing in a chicken an immune response conferring protection against infection by *Eimeria necatrix* or *Eimeria tenella*. The protein has a molecular weight of about 26,000 and is composed of two polypeptides joined by a disulfide bond. The two polypeptide subunits have molecular weights of about 18,000 and about 8,000, respectively. The gene encoding the protein has been sequenced and the amino acid sequence of the protein deduced therefrom.

The protein and antigenic polypeptides having an amino acid sequence included within the protein may be incorporated into a vaccine for conferring upon a chicken active immunity against infection by *E. necatrix* or *E. tenella*.

1 Claim, 10 Drawing Sheets

Figure 1: Amino Acid Sequence of the 17,000 Dalton Polypeptide Component of the TA4 Antigen

```
[gln]asp tyr pro thr ala val thr leu asp(cys)lys(glu)ala
     |------------------PAP---------------------------->
                                       |-----CH3----------
                                                       |V7 met asn lys leu arg lys ala ala gly leu pro ala phe glu asp ala val gly
------------------------CH3-----------------------------------------------
----------------------------V7--------------------------------------------
    |------------------------CN1------------------------------------------- asp thr phe val leu pro ala tyr(ser his)glu glu ser arg ala ala pro val
--CH3-----| |------------------------CH2'---------------------------------
---------V7------------------>                       |---------V6---------
-------------------------CN1----------------------------------------->
                                                         |----R2--------- ala glu thr leu trp lys thr glu ile cys pro lys val leu gly gly gly arg
---CH2'--->                        |-------------------V4-----------------
-V6---| |-------------------------------V2--------------------------------
-------------------------------R2-----------------------------------------
                                                     |------CH5----- ser arg asn val thr glu ala val lys leu thr gly asn phe ala tyr tyr pro
----------V4-----------| |----------------------V5------------------------
---------V2------------| |----------------------V1------------------------
--R2--|
             ----------------CH5----------------------->
|-------------------------------R1---------------------------- val thr asp gly lys lys glu cys ser asp ala val glu tyr trp lys gly gly
----------V5----------------|                                |---CH2----
-------------------------V1-----------------------------------------------
-------------------------R1---------------------------------->  |--R4-- leu ser gln phe asn asp thr ile pro pro thr phe gln ala leu asn asp pro
-------------------------------CH2--------------------------------------->
----------V1---------------->
-------------------------------R4-----------------------------------------
                                                         |---R2'---- val val tyr asn asp arg ala val ser phe val ala leu tyr asn pro lys thr
--------R4-------------------->     |------------CH1----------------------
          |----------CH4-------------|
------------------R2'-----------------------------------------------------> ser pro val val ser(cys)val leu leu gln(cys)pro asn ala gly val gly gly
-------------------------------CH1---------------------------------------|
```

> indicates peptide sequence may continue, but too weak to follow
| indicates peptide C-terminus
() probable amino acids confirmed by DNA sequence
' indicates secondary sequence
CN: cyanogen bromide fragment; CH: chymotrypsin fragment; R: Arg-C fragment; V: V8 fragment; PAP: pyroglutamate aminopeptidase treated 17kd protein.

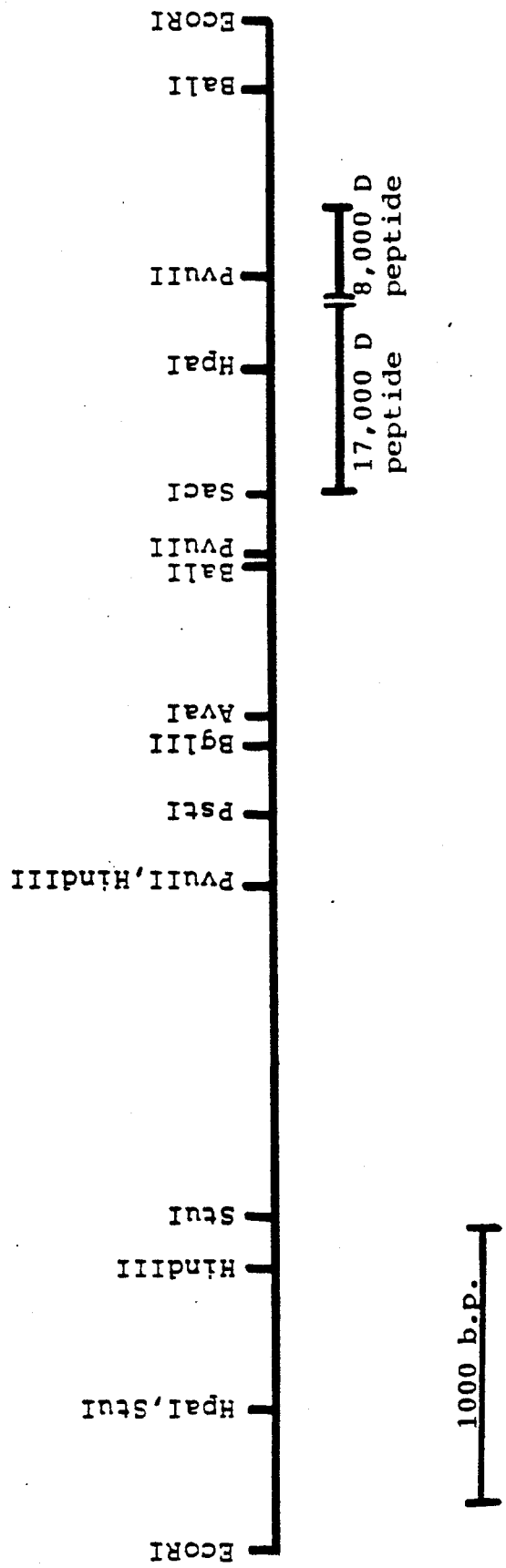
Figure 2. Restriction Map of the 5.5 kb Insert of Clone 108-1.
PstI and BalI sites shown are the rightmost sites, but not the only sites.
No sites for BamHI, EcoRV, NruI, SalI, SmaI and PvuI.

Figure 3a

```
                                    AGATCTATCAAGCAATAATCATCTA
CCTCCAAATATATGCTATGAAATGC7AAATTGCGTGAGAGTGATTCGTCACAGCAACGTC
TCATGCAGAGTGCCCGAGAACTGA5GGGAGAAACAGTGGAGTGACCGCGGGTCGCTGGTA
TTTTCTTGCTTTCATTGGCAAACGYGGCATTTTCAAGTGCCATTTTTCTTGTAATCACAT
TAGTTTGCCAGTAAATGAGGGGAATATTCTGGTGTAAGCTGTTCTTCTGGCAGTTTCACG
AGAGTCACACCGTCACCTGGOAGGTAACCTGGAAAGGGGCGGTGGCAGGAATGGCGCAAG
GCATGGAACAATGAAAGCTGAGAGCAGCGTCAAA3GGATGAATTTTCAATTTCACGTTTG
CCCTTAAATCCATTCAAGTGGGCCGAGACCGCTCTCGGAAGYGCAGTCTCGTTTGCGATT
GCATTMCCTGCACACACCTATGACGACGTACGGTGTTGGGCAGAACCTGAACATAGCGTT
TACGTCTAMAGCCGCAGCCCAAAGAAACTCTGCATACTTTTGCCAAGATATTTCAAATAA
AACCTCTTTGCCGAATTGTATTTTCACCCTCTATCTACTATTTCCTGCCCACTATGAGAG
GCAGCAAGC7GTAGCGTGCCTTCCAATGGCCAGCACCAGCGCGCCAG7TAGGGCAGCAGC
TGTCAACCTCGCTGTCATCTGTCAACAGGCCGCCAGAACTCTTCCCATATCTGTCAAAAC
ATATTTATCTGCTCACTTTACAGTTTCTGTACAGTCACTTTTGCATATTATACAATTACT

MetAlaArgLeuSerPheValSerLeuLeuSerLeuSer
GTACAGTCATATTTGCTCAAAATGGCTCGTCTTTCTTTTGTTTCTCTTCTTTCTCTGTCA
                                     *
LeuLeuPheGlyGlnGlnAlaValArgAlaGlnAspTyrProThrAlaV<----------
CTGCTCTTCGGGCAGCAAGCAGTCAGAGCTCAGGATTACCCAACAGCAGGTGGGCTTTTC

---------------Intron A----------------------------
CGCTAGCTGTTTTTGGTCCGATAGCATCGGAGCATCTCCCAAAACGAGGTGCATTCACC -------------------------------->alThrLeuAspCysLysGluAlaMetAsn
TTTTGCATGTTGTGTGCGGAAATTTTATCAGTTACGCTGGACTGTAAAGAAGCGATGAAC LysLeuArgLysAlaAlaGlyLeuProAlaPheGluAspAlaValGlyAspThrPheVal
AAGCTGAGAAAAGCAGCAGGACTTCCTGCATTCGAAGATGCTGTGGAGACACATTTGTT LeuProAlaTyrSerHisGluGluSerArgAlaAlaProValAlaGluThrLeuTrpLys
CTACCAGCATACTCGCATGAAGAGTCTAGGGCGGCACCAGTAGCTGAAACTCTCTGGAAG ThrGluIleCysProLysValLeuGly<----------------------------
ACGGAGATATGCCCCAAAGTCTTAGGAGTAAGCCGTCCACGGCCTTGCATCGTCATGATG
```

```
-------------------Intron B----------------------------
TAGTAGGTGTTCTGAGCAGCTTCGTTCTGTGGAACAAGGAACTACACTGTCCTTGAATTT --------------------->GlyGlyArgSerArgAsnValThrGluAlaValLysLeu
TTAATCTTTTGTTACGTACAGGGCGGAAGGTCCAGGAACGTTACTGAAGCTGTCAAGTTA ThrGlyAsnPheAlaTyrTyrProValThrAspGlyLysLysGluCysSerAspAlaVal
ACTGGCAATTTTGCCTACTACCCCGTCACAGACGGCAAAAAAGAGTGCAGCGATGCTGTG GluTyrTrpLysGlyGlyLeuSerGlnPheAsnAspThrIleProProThrPheGlnAla
GAGTACTGGAAAGGCGGACTTTCTCAGTTCAACGACACAATTCCCCCAACGTTCCAAGCG LeuAsnAspProValValTyrAsnAspArgAlaValSerPheValAlaLeuTyrAsnPro
TTGAACGACCCCGTTGTGTACAATGACAGGGCTGTTTCCTTTGTCGCCCTATACAACCCC
                                                         **
LysThrSerProValValSerCysValLeuLeuGlnCysProAsnAlaGlyValGlyGly
AAAACCAGCCCCGTTGTCAGTTGCGTGCTCCTCCAGTGCCCTAATGCAGGTGTTGGTGGA +
ArgArgLeuAlaAlaGlyThrThrAspAlaValIleCysLeuThrAsnProAlaProLeu
CGCAGGCTTGCGGCAGGCACGACAGACGCTGTCATTTGCTTGACAAATCCGGCTCCTTTG GluAlaArgSerGlnProPheAs<-----------------------------------
GAAGCAAGGTCACAACCATTCGAGTGAGAGTCAGCTGGTCGCCACTGCAACATGCATCAA -------------------Intron C--------------------------
TGCGGCAGGTTACACTGGGGGTC7TGAGGTTGGTTGAAGCGCAATCTTCTAATACTTGTT ------------------------->pAspGluGlnTrpLysLysIleValAspSerLe
TGTAATGTTTGTAATGTTTGCGTGCAGCGACGAGCAATGGAAGAAAATTGTTGACTCTCT uSerLeuSerGluGluGluGluGluLysGlyGlyValSerProValValProSerValAl
ATCTCTCTCTGAGGAAGAGGAAGAGAAGGGCGGAGTTTCTCCAGTCGTCCCTTCAGTAGC ++
aLeuIleSerAlaAlaValIleSerAlaPheAlaLeuPhe
CCTCATCTCTGCGGCGGTCATCTCCGCTTTCGCTCTCTTTTAGGCGGGCGCCGGTTGTTA

GTGACACACCAGCATTGGACAGATATGGCGGCGCAAGTTCCTTCCTGAGTGAAATCCTTG

AGTGACAAACGAGCACCTCTCCTGGACGAAATGTGATGAATTAAGACAGCTTTGGTTGTT

TGAAGTGTATGCAAAAGCTACATTTGTAGGGCCCTTTTATAGGATAATCGGAGGAAGCGC

AATTTTATTTAAAACCCTTGCAGAGAGTCGCCACGTGCGAGTGCAAGTGTTGCGCAGTGT

GTGCTGCCAAATGAAATTCTCGATCTTTAGTGTACTCAAGCCAGAAGTTTCGGCGTTGAT

GTACCCGCCGGTGGTATCTGCCATGCCATGCCTGCCTGTTTGGGCAGTACAACCTCATAC

CAAGTGGCTTGTGTCATGGCATGTGTGGCCAAGCTACTTTTAGAGGGACAACAATGGGGA

TATTTTGAAGTATTTCGGATAAATACTCATCTGCTGTCCCTACCCACTGAGGCGCCATGG
```

Figure 3c

TGTTACCTTCCTCATTTGAAGGGGAAAACTTGGTTGATAATTTCTTGTCCTTCAACTTGT

CTTGATAAATCGAAGATTATATTGTAGATAGTATACGTGGTGAACAGTTTTTAGGGAAGA

CTGTAAACCACAAGTTAAACGTAGTCGGAATTC

Legend

* Initial amino acid of 17,000 Dalton peptide
 ** Final amino acid of 17,000 Dalton peptide
 + Initial amino acid of 8,000 Dalton peptide
 ++ Final amino acid of 8,000 Dalton peptide Key to ambiguous bases 3 = Probably C
 4 = Probably T
 5 = Probably A
 6 = Probably G
 7 = Maybe C
 8 = Maybe T
 9 = Maybe A
 0 = Maybe G R = A or G
 Y = C or T
 J = C or A
 K = T or G
 L = T or A
 M = C or G

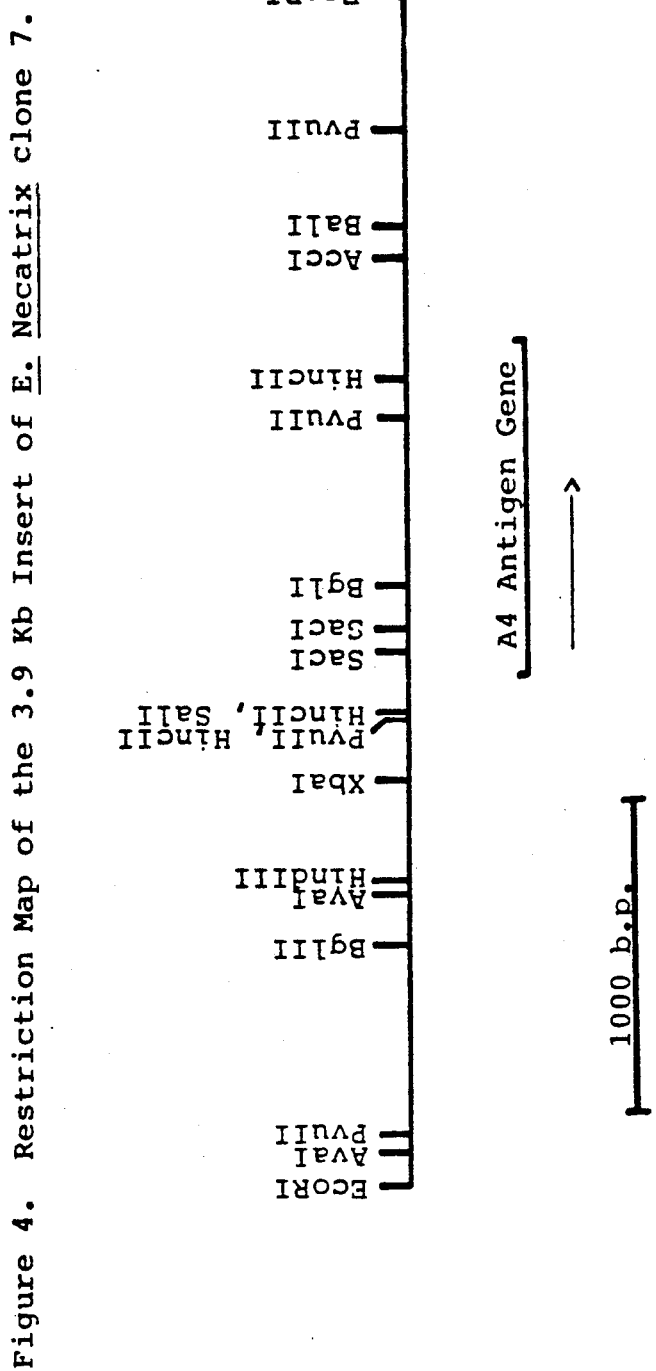
Figure 4. Restriction Map of the 3.9 Kb Insert of E. Necatrix clone 7.

Figure 5a

DNA sequence of the E. necatrix genomic clone encoding the NA4 antigen

```
CTGCTTCATGCAACGCCACATTTTCAAGCTTCACTTTTCTGATACTCACATTATTTTGCCAGCAAGAGA3GGATA

TGTTCGGTGTAAGCTGJTCTTCTGGCAGTTTCATGAGAGTGACAGCGTCACCTGGTGGTAACCTGCGCTGGGGGC

GGCGGCAGGAATGGCGCAAGGCGTGGAACAATGAACGCTGACAGGCAGCGTCAAAGAGATGAATTTTCAATTTCA

CTTTTGCCATTAAATCCATTCAAGTGGGCCGAGACCGCTTTCTGGAGTGCAGTCTCGTTTGCGTTGGCATTCCCT

GCACACACCTGATGATGACGTAGGGTGTTGCGCAGAACCTGAATATAGCGTTTAGGTCTAGAGCCGCAGCCCTAC

TAAATCTGCACATTCTTGCATGATATTTCAAATAAAACTCTTGCGAAATTATATTTTCACTTTCTATCTACTATT

TGCTGCCCACTATGCGAGGCAGCAAGCCGTAGCGTGCTTCCAATCGCCAGCACCGGCGCGCCAGCTAGGGCAGCA

GCTGTCAACCTCGCTGTCATCTGTCGACAGCCGCCACAACTCTTTTCATATCTGTCAAAACATATTTATCTGCAT
                                                                                     MetAlaArgLeu
TTTACAGTTTCTGTACAGTCATTTTTGCATTTTATAGTTACTGTACAGTCATATTTGCTCAAAATGGCTCGTCTC
                                                                                               *
SerPheValSerLeuLeuSerLeuSerLeuLeuPheGlyGlnGlnAlaAlaArgAlaGlnGluThrTyrProThr
TCTTTTGTTTCTCTTCTTTCTCTGTCACTGCTCTTCGGGCAGCAAGCAGCCAGAGCTCAGGAAACATACCCAACA

AlaG|————————————Intron A—————————————————————————————————————
GCAGGTGGGCTTTTCCGCTAGCCGTTTTTGGTCTGACAGCATCTGAGTACTTCCCAAAACAGCGTGCATTCTTCT ——————————————————————————|luThrMetGluCysArgGluAlaMet↑snGluLeuArgLysAlaA
TTTGCATGTTGTGTGCGGAAATTTTATCAGAAACGATGGAGTGTAGAGAGGCGATGAACGAGCTCAGAAAAGCAG laGlyLeuProGluPheGlyAsnAlaValGlyAspAlaValValLeuProAlaTyrSerHisGluAlaArgAlaA
CAGGGCTTCCTGAATTTGGAAATGCTGTTGGAGATGCAGTAGTTCTACCAGCATACTCGCACGAGGCCAGGGCGG laProValAlaGluThrLeuTrpLysThrGluIleCysProLysValLeuGly|——————————————————
CACCAGTGGCTGAAACTCTGTGGAAGACGGAAATATGTCCCAAAGTCTTAGGAGTAAGCCGTCCTCTGCATTGTA ————————————————————Intron B————————————————————————————————
GTCGTCCACTGCATTGTCATGTAGCAGGTGTTCTGAGCAGCTTATCTCTTTAAACAAGGAACTACGCCCTCCTCA ——————————————————|GlyAlaArgAlaLysSerValThrGluAlaValLysLeuThrGlyAsnPh
ATTTCTAATCTTTCGCTGCGTACAGGGAGCAAGGGCCAAGAGTGTTACCGAAGCTGTCAAGCTAACTGGCAACTT eAlaTyrTyrProValThrAspGlyLysLysGluCysSerAspAlaLeuGluTyrTrpLysGlyGlyLeuSerGl
TGCCTACTACCCCGTCACCGACGGCAAAAAAGAGTGCAGCGATGCTCTGGAGTACTGGAAAGGCGGACTTTCGCA nPheAsnAspLysIleProProThrPheGlnAlaLeuAsnAsnProAlaValTyrAsnAspArgAlaValSerPh
GTTCAACGATAAAATTCCCCCAACATTTCAAGCGTTGAACAACCCCGCTGTGTACAATGACAGGGCCGTCTCCTT eValAlaLeuTyrAsnProLysProSerProValValSerCysValLeuLeuGlnCysProAsnAlaGlyGlyGl
TGTCGCCCTATACAACCCCAAACCCAGCCCCGTTGTTAGTTGCGTACTACTCCAGTGCCCTAATGCAGGAGGTGG
```

| FIG 5 | FIG 5a | FIG 5b |

Figure 5b

```
**                  +
yGlyArgArgLeuAlaAlaGlyThrThrAspAlaValIleCysLeuThrAsnProAlaProLeuAlaAlaGlySe
TGGACGCAGGCTTGCGGCAGGCACGACAGATGCTGTCATTTGCTTGACAAACCCTGCTCCTTTGGCAGCAGGCTC rProProPheAs|------------Intron C-----------------------------------
ACCACCATTCGAGTGAGAATCAGCTGTTCGCCACTGCAACATACATCAAGCGGCAGGATACACTGGGGGCACTT ---------------------------------------------------------|pAspGluGlnTrpLysLysIl
GAGGTTGGTTGAAGCGCAATCTTCGGTGA4GCTTGTTTTGTAATTTGCGTGCAGCGACGAGCAATGGAAGAAAAT eValAspSerLeuSerGluLysLysGlyGlyValSerProValGlyProSerValAlaLeuIleSerAlaAlaVa
TGTTGACTCTCTATCTGAAAAGAAGGGTGGAGTTTCTCCAGTCGGCCCTTCAGTAGCCCTCATCTCTGCGGCGGT lIleSerAlaPheAlaLeuPheAM
TATCTCCGCTTTCGCTCTCTTCTAGGCGGGCTACACGCAGCATTGGACAGATATGGCAGCGCAAACTCCTTCCTG

AGAGAAATCCTTAAATGACAAACGAGCACCTCTCCTGGACGAAGTGTGATCAAGATAGCTTATAGTGCTTTTGGT

TGTTCGAAGTGAAGTATGCAAAAGCTACATTTGTAGGGCCCTTTTATAGGATAATCGGGAGGAAGCGCAATTTTA

TTTAAAACCCTTGCAGAGAGTCGCCACGTGCGAGTGCAAGTGTTGCGCAGTGTGTGCTGCCAAGTGAAATTCTCG

ATATGTAGGTGTACTCATGCCAGAAGTTTCGGCGTTGATGTACCCACCGGTGGTATACGCCATGCCACGCCTGCC

TGTTTGGGCAGTACAACCTCATACCAAATGGGCATGCTTGTGTCACTGCACGTTTCTGTATCATTAGTGGCCAAG

CAACTGTTTAAAGGGGAAGCAGTGGGGATATTTTGAAGTATTTTGAATAAATACTTTATTTGCTATACCCACCCG

CTGAGGCGCCATGGTGTTGCTGTCCTCATTTGAAGGGGAGAAACTGATTGATAATTTCCTTGTCCTTCAACTTGT

CTTGGTAAATCGAGGAATACGTAGTGAGC3ATTTTTTAGGGAAGATTGTAAACCACAGTAAAACGTTTAGCCGAC

ATTTTCTACACTCGTACGTCGGAAAAGCGCATAAGCTAGA
```

LEGEND
| Nucleotide | Definitely | Probably |
|---|---|---|
| cytosine | C | 3 |
| thymine | T | 4 |
| adenine | A | 5 |
| guanine | G | 6 |
| unknown | N | N |

Either
    C or A    J
    T or A    L

\* Putative initial amino acid of 18,000 dalton peptide
\*\* Putative final amino acid of 18,000 dalton peptide
+ Putative initial amino acid of 8,000 dalton peptide Figure 6. Amino Acid Sequence Homology Between E. tenella and E. necatrix A4 Antigens

```
                                   +
                    Exon 1 <------|------> Exon 2
E. tenella  MARLSFVSLLSLSLLFGQQAVRAQD YPTAVTLDCKEAMNKLRKAAGLPAFEDAVGDTFVLPAYSHEESRAA
            ******************** ***  ****  *  * **** ********  ****  *******  ***
E. necatrix MARLSFVSLLSLSLLFGQQAARAQETYPTAETMECREAMNELRKAAGLPEFGNAVGDAVVLPAYSHEA RAA Exon 2 <------\------> Exon 3
            PVAETLKTEICPKVLGGGRSRNVTEAVKLTGNFAYYPVTDGKKECSDAVEYWKGGLSQFNDTIPPTFQALN
            ******************  *  ******************** *************  ********
            PVAETLKTEICPKVLGGARAKSVTEAVKLTGNFAYYPVTDGKKECSDALEYWKGGLSQFNDKIPPTFQALN ‡         Exon 3 <------|------
            DPVVYNDRAVSFVALYNPKTSPVVSCVLLQCPNAGVGGRRLAAGTTDAVICLTNPAPLEARSQPFDDEQWKK
             *  ***************  ******************* ******************  * ********
            NPAVYNDRAVSFVALYNPKPSPVVSCVLLQCPNAGGGGRRLAAGTTDAVICLTNPAPLAAGSPPFDDEQWKK ---> Exon 4
            IVDSLSLSEEEEEKGGVSPVVPSVALISAAVISAFALF
            ******   * ******* ******************
            IVDSLS    EKKGGVSPVGPSVALISAAVISAFALF
```

* = Homologous amino acid
+ = Start of E. tenella 17,000 dalton polypeptide component of the A4 antigen
‡ = Start of E. tenella 8,000 dalton polypeptide component of the A4 antigen

| | | | |
|---|---|---|---|
| C = Cys | A = Ala | F = Phe | D = Asp |
| H = His | G = Gly | R = Arg | N = Asn |
| I = Ile | L = Leu | Y = Tyr | B = Asx |
| M = Met | P = Pro | W = Trp | E = Glu |
| S = Ser | T = Thr | | Q = Gln |
| V = Val | | | Z = Glx |
| | | | K = Lys |

Space in E. tenella amino acid sequence = additional amino acid in E. necatrix sequence compared to E. tenella sequence.

Space in E. necatrix amino acid sequence = amino acids not in E. necatrix sequence compared to E. tenella sequence.

Figure 7. Comparison Of The Three Introns Within The Gene Encoding The A4 Antigen In
E. tenella and E. necatrix Alignment of Intron A from E. tenella with Intron A from E. necatrix

```
E. tenella   1 GTGGGCTTTTCCGCTAGCTGTTTTTGGTCCGATAGCATCGGAGCATCTCCCAAAACGAGGTGCATTCACCT
               ******************** ********** ** ****** *** * ********* ********* **
E. necatrix  1 GTGGGCTTTTCCGCTAGCCGTTTTTGGTCTGACAGCATCTGAGTACTTCCCAAAACAGCGTGCATTCTTCT 73 TTTGCATGTTGTGTGCGGAAATTTTATCAG
               ******************************
            73 TTTGCATGTTGTGTGCGGAAATTTTATCAG
```

Alignment of Intron B from E. tenella with Intron B from E. necatrix

```
E. tenella   1 GTAAGCCGTCCACGGCCTTGCA TCGTC          ATGATGTAGTAGGTGTTCTGAGCAGCTTCGTTCTG
               *********** * ** *** * *****         * ****** ******************  ***
E. necatrix  1 GTAAGCCGTCCTCTGCATTGTAGTCGTCCACTGCATTGTCATGTAGCAGGTGTTCTGAGCAGCTTATCTCTT 73 TGGAACAAGGAACTACACTGTCCTTGAATTTTTAATCTTTTGTTACGTACAG
               ************** * *** * *** ****** * * *******
            73 TAAACAAGGAACTACGCCCTCC TCAATTTCTAATCTTTCGCTGCGTACAG
```

Alignment of Intron C from E. tenella with Intron C from E. necatrix

```
E. tenella   1 GTGAGAGTCAGCTGGTCGCCACTGCAACATGCATCAATGCGGCAGGTTACACTGGGGG TC7TGAGGTTGGT
               ****** ****** **************** ****** ******* ************ * **********
E. necatrix  1 GTGAGAATCAGCTGTTCGCCACTGCAACATACATCAALGCGGCAGGATACACTGGGGGCACTTGAGGTTGGT 73 TGAAGCGCAATCTTCTAATACTTGTTTGTAATGTTTGTAATGTTTGCGTGCAG
               **************       *       ****   *********
            73 TGAAGCGCAATCTTC       GGTGA4GCTTGTTTTGTAA   TTTGCGTGCAG
```

Legend

\* = Homology

Space in E. tenella DNA sequence = additional base in E. necatrix sequence compared to
E. tenella sequence.

Space in E. necatrix DNA sequence = base not in E. necatrix sequence compared to E.
tenella sequence.

Key To Ambiguous Bases

4 = Probably T
7 = Maybe C
L = T or A

ANTIGENIC PROTEINS AND VACCINES CONTAINING THEM FOR PREVENTION OF COCCIDIOSIS CAUSED BY EIMERIA *EIMERIA NECATRIX* AND *EIMERIA TENELLA*

BACKGROUND OF THE INVENTION

Throughout this application, various publications are referenced by Arabic numerals within parentheses. Full citations for these references may be found at the end of the specification immediately preceding the claims. The disclosures of these publications in their entireties are hereby incorporated by reference into this application in order to more fully describe the state of the art as known to those skilled therein as of the date of the invention described and claimed herein.

The phylum Apicomplexa includes hundreds of different organisms belonging to the order Eucoccidiorida. The genus is included within the order of true coccidian agents. Of the organisms belonging to this genus, several species are of recognized importance to the chicken industry. These species include *Eimeria tenella, E. maxima, E. acervulina, E. necatrix, E. brunetti, E. mivati E. mitis* and *E. praecox.*

Differentiation of species is based on the site of infection within the host and oocyst morphology. To date, biochemical markers have not been used for speciation, although differences have been noted for each of the above species. For Eimeria, the entire life cycle is completed within a single host. The actual stages of the life cycle vary in complexity depending upon the Eimeria species involved. For example, *E. necatrix* has a complex life cycle pattern. Upon being ingested in contaminated feces, food or water, sporulated oocysts excyst within the digestive tract as a result of the combined action of mechanical shearing and enzymatic hydrolysis of the sporocyst cap. The liberated sporozoites traverse epithelial cells within specific regions of the intestine. Development begins within the Crypt of Lieberkuhn to the level of first generation meronts; the meront is a transitional stage consisting of rounded organisms with a more pronounced nucleus, plus increased energy generating and protein synthesizing capacity. Development of first-generation merozoites follows due to multiple fission of meronts. The release of first-generation merozoites destroys the host cell, and the parasites migrate to infect new host cells undergoing a second asexual cycle. Meronts develop to the level of second-generation merozoites destroying additional epithelial cells as they are released. Further destruction of host cells follows with the liberation of the third-generation merozoites. Second- and third-generation merozoites may infest still another population of host enterocytes to begin the sexual phase. Sexual development commences with the production of microgametes and macrogametes through the process of gametogenesis. Liberated microgametes fertilize macrogametes to form zygotes. Development of immature oocysts is followed by rupture of the host cell. Oocysts, released into the lumen of the gut, are passed through the feces to the environment and mature (sporulate) in the presence of atmospheric oxygen.

The process of parasite development is self-limiting if the host ingests no additional oocysts. However, this proves to be an unrealistic expectation in crowded poultry houses. Disease due to *E. necatrix* can result in severe economic losses associated with diminished feed efficiency and pathologic manifestations.

The pathology of coccidiosis due to *E. necatrix* and some other species is in large part related to the rupture of host cells during the release of merozoites. Tissues are disrupted primarily within the mid-gut subepithelium. Bleeding within the gut is related to rupture of small capillaries servicing the epithelium. It may be difficult to control the progress of disease using coccidiostats, once asexual development is established. Secondary infection often complicates the disease caused by Eimeria. Death can occur within 4-7 days in severely infected birds.

A consistent property of the coccidia is that the sporozoites initiate the infection process within very specific tissue sites (29, 34, 42). The site specificity of infection is a characteristic commonly used for speciation of Eimeria. The asexual stages of *E. necatrix* show a propensity for invasion of epithelial cells residing within the mid-intestine. Sexual stages develop primarily in the cecal pouches.

Investigation of immunity to coccidiosis has examined the role of humoral immunity, and more specifically of serum antibody. Studies have shown a lack of correlation between serum antibody and resistance to disease (44). However, most available data support the contention that a local response with involvement of the secretory immune system or cell mediated immunity (CMI), or both, are involved in the protective response.

Interference with recognition, penetration and/or attachment of pathogens to host cells has a demonstrated protective effect as shown with viral, bacterial and protozoan models. Genetic deletion of key host cell receptors or pathogen attachment features can prevent the initial colonization process (13, 41). Alternatively, secretory antibodies can interfere with the colonization process by binding to, and consequently masking requisite receptors (23, 54). More than one immunoglobulin class has been reported to have the capacity of interfering with the initial colonization process of *Eimeria tenella* (10). However, recent reports indicate that only production of secretory IgA has been correlated with natural protective immunity (9, 44). Porter and Davis (10) and others (44) reported that secretory IgA neutralizes the extracellular stages of the parasite either by significantly limiting penetration or so debilitating those organisms which did penetrate as to prevent subsequent development.

It has been estimated that an amount approaching $0.5-1.0 billion is spent annually by producers worldwide to combat disease, or the effort to curb the devastating effect of coccidiosis in chickens (29, 39). Currently, the most widely used means of controlling Eimeria in chickens is through the application of antiprotozoal chemical feed additives. The specific composition varies with the coccidiostat used, and each product affects only certain stages of the coccidian life cycle (29, 38, 43). Disadvantages of using coccidiostats are many, including short-term residual protection in birds, occasional diminished performance, invocation of resistance to the drug in parasites, and to some extent, safety. Products currently remain on the market for only a few years because of the development of drug resistant strains. This adds considerable pressure on the cost of development and continued manufacture of efficacious products (38).

Protection of birds by immunization has met with some success. Investigators have been able to invoke limited protection using preparations of killed organisms (1, 31, 32). A more effective approach for immunization of chickens has been with the use of a live protozoal product - - - e.g. Cocciac TM (12). The product, being a multivalent composition containing low doses of viable oocysts, is administered in drinking water to invoke a mild parasitemia in birds. A drawback of this product has been occasional depressed performance of birds during the first weeks following administration. Variables such as excessive dosing or moisture content of bedding have even led to severe outbreaks of coccidiosis. See also, U.S. Pat. No. 3,147,186 (1964) which concerns the use of viable, sporulated oocysts of E. tenella to immunize chickens and U.S. Pat. No. 4,301,148 (1981) which concerns the use of sporozoites of E. tenella for the same purpose.

An alternative means of introducing the live vaccine into broiler houses is by way of the feed. This has been considered in a recent British patent (GB2,008,404A). Prior to mixing with the feed, fully virulent oocysts of E. tenella are encapsulated in a water soluble polysaccharide to protect against desiccation. The oocysts are in sufficient amounts only to induce subclinical infection. Though the immunizing ability was found to be excellent, no development of this method is foreseen due to questionable field acceptability. However, if attenuated strains of all the important coccidia could be developed, the procedure may be more acceptable.

Efforts have indeed been made to develop Eimeria lines of reduced virulence. Some species have been successfully attenuated through chicken embryo passage (14, 27, 30, 48). These strains have diminished ability to cause disease, yet have retained sufficient immunogenicity to invoke immunity. Some problems do, however, remain with the handling of these strains. As examples, the attenuated variants of E. necatrix have a critical passage limit whereby more or less embryo passage can result in loss of immunogenicity or maintenance of the original virulent form. Furthermore, some attenuated organisms revert to the virulent form upon minimal back-passage through chickens (28, 50). Thus, problems associated with maintaining consistent properties in attenuated organisms are apparent.

Attenuation by precocious selection has also been practiced when Eimeria strains cannot be readily passaged through embryonated eggs. In this process, shed oocysts are harvested late in the prepatent period prior to the onset of heavy oocysts shedding (19, 35, 37, 49). Such selection results in cultures having abbreviated life cycles, and a corresponding diminution in virulence properties (19, 35, 37, 49). Though the trait of precocity for E. tenella (20) and E. acervulina (36) has been demonstrated to be genetically stable, not enough information is known about this method to assess its usefulness as a tool in the poultry industry.

There is little information available about the surface antigen composition of avian coccidia. Hybridoma cell lines which secrete monoclonal antibodies directed to antigens on the surface of sporozoites of Eimeria tenella have been reported (59). The antigens were not identified, other than that their molecular weights were between 13 and 150 kilodaltons. Moreover, no biological significance or described efficacy in a vaccine was attributed to the antigens. Previous work in the laboratory of M.H. Wisher suggests the presence of approximately 16 polypeptides identified by surface iodination of excysted sporozoites of E. tenella and having molecular weights form 20,000 to greater than 200,000 (58).

Subunit approaches to vaccine development have proven successful over the past few years. In such approaches, candidate protective antigens are identified and characterized for the purpose of eventual preparation on a large scale. In studying parasite antigens, one research group used monoclonal antibodies to identify a potential protective antigen on the surface of Babesia bovis (60). A B. bovis antigen of 44,000 daltons has been identified, which when purified and injected into experimental animals afforded some level of protection against primary challenge. An immunologically important 30,000 dalton protein of Toxoplasma gondii has also been identified using monoclonal antibodies (22).

Since mid-1981, Danforth and coworkers have published several papers in which they indicate the possibility of producing monoclonal antibodies toward antigens of avian Eimeria species (6, 7, 8). Similarly, Speer, et al. (51, 52) have demonstrated the development of hybridomas against E. tenella and some physiologic properties thereof. Antibody-secreting hybridomas have been selected on the basis of an indirect fluorescent antibody test (7). The patterns of reaction, as observed with ultraviolet microscopy, have varied depending upon the monoclonal antibody used. Patterns have included exclusive reaction with sporozoites only vs reaction with sporozoites and merozoites; staining of the anterior portion of the sporozoite the entire membrane; and staining of distinct internal organelles vs nondescript internal staining (8).

Although the preparation of murine-origin hybridomas producing monoclonal antibodies is commonly practiced by those familiar with the art, there is nothing to suggest that the direct and specific selection of sporozoite-neutralizing hybridomas, against the species E. necatrix will subsequently identify virulence determinants of E. necatrix useful in the development of a subunit vaccine.

This invention concerns the identification, characterization, preparation and use of polypeptide antigens for development of immunity to coccidiosis by Eimeria necatrix and Eimeria tenella.

The antigens are capable of being precisely dispensed in terms of direct antigenic content and cannot cause disease thus avoiding vaccine strain-related outbreaks and reversions or changes in immunologic properties.

SUMMARY OF THE INVENTION

A purified antigenic protein, also referred to herein as the NA4 protein or NA4 antigen, has been isolated from Eimeria necatrix. It is capable of inducing in a chicken an immune response conferring protection against infection by Eimeria necatrix or Eimeria tenella. A homologous antigen found on E. tenella is referred to as the TA4 antigen. The NA4 protein has a molecular weight of about 26,000 daltons and is composed of two polypeptides joined by a disulfide bond. One of the polypeptides is characterized by a molecular weight of about 18,000 and by a blocked N-terminal amino acid; the other polypeptide is characterized by a molecular weight of about 8,000. The amino acid sequences of both polypeptides are as set forth in FIG. 5.

The purified antigenic protein may be prepared by separately recovering it from the sporocyst of E. necatrix. Thus, antigen recovery may be effected by immunoaffinity chromatography or immunoprecipitation utilizing the highly specific monoclonal antibody Ptn 7.2A4/4 produced by hybridoma cell line ATCC No. HB8561. Alternatively, the protein may be prepared by introducing DNA encoding the protein into a suitable host in which the DNA is expressed and from which the protein may be recovered.

Active immunity against infection by *E. necatrix* and *E. tenella* may be conferred upon a chicken by administering to the chicken an effective-immunizing amount of the antigenic protein. Preferably, the protein or a fragment thereof is incorporated into a vaccine with a suitable carrier and suitable doses of the vaccine administered to the non-immune chicken.

BRIEF DESCRIPTION OF THE FIGURES

FIG. 1 displays the amino acid sequence of the 17,000 dalton polypeptide component of the *E. tenella* (TA4) antigen determined by microsequencing. FIG. 1 also shows the overlapping peptides produced by various chemical and enzymatic digestions.

FIG. 2 shows the restriction enzyme map of the *E. tenella* genomic clone 108-1 encoding the TA4 antigen. FIG. 2 also shows the position and orientation of the gene for the TA4 antigen within the 5500 bp *E. tenella* ecoRI DNA fragment.

FIG. 3 shows the DNA nucleotide sequence of the Bgl II-EcoRI DNA fragment of the genomic clone 108-1 depicted in FIG. 2. In addition, FIG. 3 shows the amino acid sequence for the signal peptide and the 17,000 dalton and the 8,000 dalton polypeptide components of the TA4 antigen. FIG. 3 also shows the introns within the gene.

FIG. 4 displays the restriction enzyme map of the *E. necatrix* genomic clone 7-49 encoding the NA4 antigen. FIG. 4 also shows the position and orientation of the gene for the NA4 antigen within the 3900 bp *E. necatrix* EcoRI DNA fragment.

FIG. 5 shows the DNA nucleotide sequence of 2440 bases of the genomic clone 7-49 depicted in FIG. 4. This sequence includes the entire HindIII-BalI region shown in FIG. 4. FIG. 5 also shows the amino acid sequence inferred for the *E. necatrix* NA4 antigen.

FIG. 6 shows the amino acid sequence homology between TA4 and NA4 antigens.

FIG. 7 displays the homology of the three introns within the *E. tenella* and *E. necatrix* genes encoding the TA4 and NA4 antigens respectively.

DETAILED DESCRIPTION OF THE INVENTION

The present invention provides a purified antigenic protein (hereinafter referred to as NA4) capable of inducing in a chicken an immune response conferring protection against infection by *Eimeria necatrix* or *Eimeria tenella*, the protein having a molecular weight of about 26,000 daltons and being composed of two polypeptides joined by a disulfide bond, one of the polypeptides being characterized by a molecular weight of about 18,000 daltons and by a blocked N-terminal amino acid and the other of the polypeptides being characterized by a molecular weight of about 8,000 daltons.

Antigenic analogs of the 26,000 dalton antigenic protein or of its 18,000 dalton and 8,000 dalton polypeptide components are also contemplated. The term "analog" as used herein means any polypeptide, which has an amino acid sequence that differs from that depicted for the 26,000 dalton protein and the 18,000 and 8,000 dalton polypeptides in FIG. 5 as a result of substitution of one or more amino acids. Such an analog is contemplated as retaining antigenic properties in that it is capable of inducing an immune response conferring protection against *E. necatrix* or *E. tenella*.

The NA4 protein is prepared by first contacting sporocysts of *Eimeria necatrix* with a detergent under suitable non-reducing conditions in the presence of protease inhibitors so as to solubilize the sporocyst membrane proteins. Next, the protein is separately recovered from the solubilized, sporocyst membrane proteins under suitable non-reducing conditions. The recovery may be effected by partially purifying the solubilized sporocyst membrane proteins by chromatography on DEAE-HPLC followed by preparative SDS gel electrophoresis under suitable non-reducing conditions. The recovery may also be effected by immunoprecipitation or immunoaffinity chromatography with monoclonal antibody Ptn 7.2A4/4 (ATCC No. HB8561).

The present invention contemplates an antigenic polypeptide having an amino acid sequence included within the amino acid sequence of the 26,000 dalton NA4 protein, which is capable of inducing in a chicken an immune response conferring protection against infection by *Eimeria necatrix* and *Eimeria tenella*. Such polypeptides include all amino acid sequences which contain an antigenic determinant from the NA4 protein and which are capable of inducing an immune response. Analogs of this polypeptide and monoclonal antibodies directed against it are contemplated. Anti-idiotypic antibodies directed against the monoclonal antibodies are also contemplated.

Antigenic polypeptides which include an amino acid sequence present in the NA4 protein may be produced by various methods, e.g., may be chemically or enzymatically synthesized, may be produced by recombinant DNA methods, may be prepared from the NA4 antigen or may be prepared from the sporocyst or sporozoite of *E. necatrix*. It should be understood that "antigenic polypeptide" as the term is used herein includes preparations prepared under non-reducing conditions as described herein, characterized by the presence within the preparation of a polypeptide having a defined apparent molecular weight on SDS-PAGE under reducing conditions. When present in such preparations, the polypeptide may be bound to another component or components, e.g. to another polypeptide by one or more disulfide bonds or two or more regions within the polypeptide may be bound to one another, e.g. by a disulfide bond. For those preparations characterized by the presence within them of polypeptides with apparent molecular weights of 18,000 or less on SDS-PAGE under reducing conditions the term "fragment" is also used to describe such preparations on the assumption that the preparations include amino acid sequences contained within the complete NA4 protein, but not the intact protein. In addition the term "fragment" is used to describe amino acid sequences derived from the NA4 protein by proteolytic digestion.

The antigens of this invention in addition to an amino acid sequence included within the amino acid sequence of the NA4 protein may contain one or more other substances such as polysaccharides, e.g. dextran, or other amino acid sequences, i.e. amino acid sequences not included within the amino acid sequence set forth in FIG. 5.

Also contemplated is a fused antigenic polypeptide having an amino acid sequence which includes the amino acid sequence of the 26,000 dalton NA4 protein and an additional amino acid sequence, which is capable of inducing in a chicken an immune response conferring protection against infection by *Eimeria necatrix* and *Eimeria tenella*. Analogs of this polypeptide and monoclonal antibodies directed against it are contemplated. Anti-idiotypic antibodies directed against the monoclonal antibodies are also contemplated.

The 18,000 dalton polypeptide of the NA4 antigen may be prepared by first contacting sporocysts of *Eimeria necatrix* with a detergent under suitable conditions in the presence of protease inhibitors so as to solubilize the sporocyst membrane proteins. Then, separately recovering the polypeptide from the solubilized, sporocyst membrane proteins under suitable reducing conditions This recovery step may involve partial purification of the solubilized sporocyst membrane proteins by chromatography on DEAE-HPLC chromatography followed by preparative SDS gel electrophoresis under suitable reducing conditions.

The present invention contemplates an antigenic polypeptide which has the amino acid sequence of the 18,000 dalton polypeptide of the NA4 antigen which itself is capable of inducing in a chicken an immune response conferring protection against infection by *Eimeria necatrix* and *Eimeria tenella*. Also contemplated are antigenic polypeptides which are fragments of the 18,000 dalton polypeptide or those which consist of the 18,000 dalton polypeptide fused to an additional amino acid sequence. Antigenic analogs of each of these fragments as well as anti-idiotypic antibodies developed against each fragment are also contemplated.

Another method of preparing the NA4 protein comprises preparing a DNA molecule coding for the protein, inserting the DNA molecule into an appropriate expression vector, e.g. a vector containing the λPL or lac promoter introducing the resulting expression vector into a suitable host, e.g. *E. coli*, under appropriate conditions permitting expression of the DNA and production of the protein and recovering the protein so produced.

Another method of preparing the 18,000 dalton polypeptide of the NA4 antigen comprises preparing a DNA molecule coding for the polypeptide, inserting the DNA molecule into an appropriate expression vector, introducing the resulting expression vector, e.9. a vector containing the λPL or lac promoter into a suitable host, e.g. *E. coli*, under appropriate conditions permitting expression of the DNA and production of the polypeptide and recovering the polypeptide so produced.

Messenger RNA may be isolated from sporocysts at many points during the sporulation process. These mRNA samples may then be translated using in vitro (33) or in vivo systems. The translation products may then be immunoprecipitated using the monoclonal antibody (Ptn 7.2A4/4). The mRNA preparation encoding the NA4 antigen may then be used to produce double-stranded cDNA (33). This cDNA may then be inserted into an appropriate cloning vector which may then be used to transform *E. coli* to generate a cDNA library. This cDNA library may then be screened by colony hybridization techniques using isotopically-labelled oligonucleotide probes whose construction is based upon amino acid sequence information from the 18,000 dalton polypeptide component of the NA4 antigen. Vector DNA from bacterial colonies containing nucleotide sequences for the 18,000 dalton polypeptide may then be isolated and the inserted coccidial DNA sequenced (45).

The present invention provides an antigenic polypeptide which has the amino acid sequence of the 8,000 dalton polypeptide component of the NA4 antigen and which is capable of inducing in a chicken an immune response conferring protection against infection by *Eimeria necatrix* or *Eimeria tenella*. Also contemplated are antigenic polypeptides which are fragments of the 8,000 dalton polypeptide or those which consist of the 18,000 dalton polypeptide fused to an additional amino acid sequence. Antigenic analogs of each of these fragments as well as monoclonal antibodies directed against each fragment are contemplated. Anti-idiotypic antibodies directed against the monoclonal antibodies are also contemplated.

A method of conferring upon a chicken active immunity against infection by either *Eimeria necatrix* or *Eimeria tenella* or a combination of both comprises administering to a chicken an effective immunizing amount of the NA4 protein, the 18,000 dalton polypeptide, the 8,000 dalton polypeptide, fragments thereof, fusion products thereof, or analogs thereof. Each of these different antigens may be used alone or in combination with one or more of the other antigens. Administration of these materials may be used to increase a relatively low level of immunity in a chicken previously exposed to *E. tenella* or *E. necatrix* and may be used in booster vaccinations.

The NA4 antigen or any of the antigenic polypeptides of this invention may be administered to chickens by any of a number of well known methods. Desirably, the administration may involve subcutaneous or intramuscular injection at the back of the neck. The amount of antigen comprising an effective immunizing amount may be any amount from about 0.1 microgram to about 1 mg. The amount of antigen is desirably above about 10 micrograms. The preferred amount of antigen is about 500 micrograms per kilogram of body weight. Alternatively, the administration may be oral (e.g., via capsule) or desirably by injection (e.g., subcutaneous, intradermal, or preferably intramuscular injection). If the mode of administration involves injection, any pharmaceutically acceptable carrier may be employed. Suitable carriers include 0.01 to 0.1 M, preferably 0.05 M, phosphate buffer or 0.8 percent saline.

A vaccine for conferring upon a chicken active immunity against infection by either *Eimeria necatrix* or *Eimeria tenella* or a combination of both comprises per dose an effective immunizing amount of the NA4 protein, the 18,000 dalton polypeptide, the 8,000 dalton polypeptide, fragments thereof, fusion products thereof, or analogs thereof and a suitable carrier. Each different antigen may be used alone or in combination with one or more of the other antigens. An effective immunizing amount is typically above about 0.1 microgram/kg of body weight of the chicken. A method of protecting a chicken against infection by either *Eimeria necatrix* or *Eimeria tenella* or a combination of both comprises administering to the chicken a suitable dose of this vaccine.

In addition, the carrier desirably also contains a preservative. One particularly suitable preservative is thimerosal (sodium ethylmercurithiosalicylate) which has activity as both a bacteriostat and fungistat. Desirably thimerosal is present in the vaccine in a final concentration of $10^{-4}$ percent.

Furthermore, the carrier desirably also contains an immunopotentiator. Various immunopotentiators known in the art may be used. The adjuvant presently employed is 94% Drakeol 6-VR, 5% Arlacel A, 1% Tween-80. Arlacel A is a mannide monoleate (Sandria Corp.). It is an irritant which has strong immunopotentiating activity when combined with antigens. Drakeol 6-VR is a hypoallergenic light mineral oil product (Penreco Corp.). Tween-80 is a monoleate derivative of polyoxyethylsorbitan and possesses detergent properties. Other suitable carriers or immunopotentiators include aluminum potassium sulfate, aluminum hydroxide, lymphokines and water in oil emulsions.

By administering a suitable dose of such a vaccine to a chicken, the chicken is protected against infection by *E. necatrix* or *E. tenella*. The amount of antigenic material per dose should be sufficient to induce production of antibodies to the antigenic material in an animal to which the vaccine is administered. To provide a sufficient degree of immunological response as measured by antibody production and protection, the amount of the antigenic material per dose is desirably above about 20.0 micrograms/kg of body weight of the vaccinated animal. Thus, the amount of antigenic material based upon a 50 gram day-old chick would be above about 1.0 microgram. Presently preferred is a vaccine containing 10 micrograms of antigenic material. In general, the antigen will comprise on a weight basis from about 0.002 percent up to about 0.2 percent of the vaccine and the dose volume will be about 0.1 ml.

This invention also provides the nucleic acid molecule which encodes the NA4 protein and which has the nucleic acid sequence set forth in FIG. 5. This nucleic acid molecule may be inserted into a cloning vehicle which may then be inserted into a suitable host cell. A suitable host cell would be a eucaryotic cell, such as a yeast cell or a mammalian cell.

A method of producing the NA4 protein comprises growing host cells having the above-mentioned cloning vehicle inserted under suitable conditions permitting production of the protein and recovering the protein so produced.

Also contemplated is a protein having essentially the same amino acid sequence as the NA4 protein but differing because of expression in a bacterial or other foreign host.

In a further embodiment a composite structure having spatial features common with those of the principal protective structures of the NA4 antigen is substituted for the previously described antigens. One such composition includes an anti-idiotypic antibody developed against the structures of an antibody to the NA4 protein or to one of the antigenic polypeptides of this invention, e.g. the monoclonal antibody Ptn 7.2A4/4, which structures confer specificity toward the respective antigen determinant. Such anti-idiotype antibodies can in themselves be monoclonal in nature, or can be raised as polyclonal antibodies. In the former example, the antibody Ptn 7.2A4/4 can be recovered from hybridoma cell line ATCC No. HB8561, purified and covalently attached to any suitable carrier protein, e.g. the key-hole limpet hemocyanin (KLH). The purified antibody, preferably the purified antibody-KLH complex, is repeatedly injected, preferably with an adjuvant such as Freund's complete adjuvant, into a suitable mammalian lymphocyte donor with Balb/C strain mice as the preferred donor. Hybridomas are developed from lymphocytes of the immunized mice. The hybridomas are screened for antibodies which compete with the NA4 antigen for reaction with the monoclonal antibody Ptn 7.2A4/4, but recognize neither the NA4 antigen nor murine immunoglobulin other than Ptn 7.2A4/4. Such hybridomas secreting anti-idiotype antibodies toward monoclonal antibody Ptn 7.2A4/4 are further expanded and cloned. Production of anti-idiotype antibody can be performed by cultures of cells in any medium suitable for growth of hybridomas and expression of monoclonal antibodies, or growth of antibody producing hybridomas in host animals, with Balb/C mice as the preferred vehicle.

Anti-idiotype antibodies can also be produced by injection of Ptn 7.2A4/4 into animals. One preferred method is to repeatedly inject 500 micrograms of Ptn 7.2A4/4, purified and formulated in a suitable adjuvant, e.g. complete Freunds Adjuvant, into a suitable animal, e.g. a rabbit. After sufficient injections, blood serum is removed after a suitable period of time from such animals. The anti-idiotypic antibodies are then recovered from the blood serum, e.g. by adsorption against normal mouse serum proteins immobilized on an insoluble support such as Sepharose ®. Specificity of the resulting antiserum is confirmed by demonstrating reactivity with monoclonal antibody Ptn 7.2A4/4 but none against normal murine $\lambda3(k)$.

The anti-idiotype antibodies prepared as above are further purified to the level of IgG fractions. Purified anti-idiotype antibody protein may be administered by any of a number of well-known methods as described for the antigen proper.

Administering an effective amount of the anti-idiotypic antibody of this invention to a chicken provides a method of conferring upon the chicken active immunity against infection by *Eimeria necatrix* or *Eimeria tenella*. A vaccine for this purpose comprises an effective immunizing amount of the anti-idiotypic antibody and a suitable carrier. Thus, administering a suitable dose of such a vaccine to a chicken provides a method for protecting the chicken against infection by *Eimeria necatrix* or *Eimeria tenella*.

The amount of anti-idiotype antibody per dose must be sufficient to invoke production of an antibody in an animal to whom the vaccine is administered. For induction of an immunological response as measured by antibody production, the amount of anti-idiotype antibody per dose is above 50 micrograms/kg body weight of the vaccinated birds. Thus, the amount of anti-idiotype antibody administered to a 50 g day-old chick would be 2.5 micrograms. Presently preferred is a vaccine containing 25 micrograms of anti-idiotype antibody. In general, the anti-idiotype antibody will comprise on a weight basis from 0.002 percent to up to 0.2 percent of the vaccine, and the dose volume will be 0.2 cc.

A method for obtaining the DNA having the nucleic acid sequence set forth in FIG. 5 comprises isolating total genomic DNA from *Eimeria necatrix* oocysts; preparing DNA fragments from the genomic DNA so isolated; ligating the fragments so prepared into an appropriate cloning vector; subjecting the DNA of the clones so prepared to hybridization with oligonucleotides containing, or complementary to, nucleic acid sequences present within the nucleic acid sequence set forth in FIG. 5 to identify appropriate clones; and isolating from the appropriate clones DNA which encodes the protein and has the nucleic acid sequence set forth in FIG. 5.

The NA4 protein is a purified, sporozoite membrane protein derived from the sporocyst of *E. necatrix*. This protein is an antigen capable of inducing in a non-immune chicken an immune response conferring protection against infection by the intestinal parasites *E. necatrix* and *E. tenella*. Although the protein has been derived from *E. necatrix*, it is contemplated that the protein may be prepared by other methods, e.g., recombinant DNA technology or total organic synthesis and accordingly the invention is not limited to protein prepared directly from *E. necatrix* but encompasses the protein independent of its method of preparation. The protein so prepared may be identical to the structure purified from parasites, or may exist as discrete fragments of the same. It may also exist as a fusion of NA4 with homologous or heterologous sequences. Additionally, it may be presented as an analogue or as an internal image (idiotype) of the same.

The NA4 protein antigen has a molecular weight of about 26,000 and is composed of two polypeptides joined by a disulfide bond. One of the polypeptides is characterized by a molecular weight of about 18,000 and has a blocked N-terminal amino acid. A CNBr fragment of approximately 16,000 daltons has the following partial amino acid sequence: $NH_2$-? ? Leu ? Lys Ala Ala Gly Leu Pro Glu Phe Gly Asn Ala Val Gly ? Ala Val Val Leu Pro Ala Tyr Ser. The N-terminal amino acid sequence of the 8,000 dalton polypeptide is: $NH_2$- Ala Ala ? Thr? Asp Ala Val Ile Cys Leu Thr Asn Pro Ala Pro Leu Ala Ala Gly Ser Pro Pro? Phe ? Asp Glu ? Trp. The complete amino acid sequence of the NA4 protein inferred from the DNA sequence of the gene encoding the NA4 antigen is shown in FIG. 5. Genomic DNA from *E. necatrix* has been isolated and cleaved with the restriction endonuclease EcoRI. The restriction fragments were ligated into an appropriate cloning vector, λgt was λB, generating a genomic library. The genomic library was then screened by plaque hybridization with a 785bp SacI-PvuII fragment of the *E. tenella* genomic clone of FIG. 2. A genomic clone encoding the NA4 antigen has been isolated and the DNA sequence has shown the two peptides of the NA4 antigen to be encoded by a contiguous nucleotide sequence (FIG. 5). Hence the 18,000 and 8,000 dalton peptides are derived from proteolytic processing of a single 26,000 dalton peptide. In addition, the DNA sequence encodes a "signal" sequence typically found at the amino terminus of many secretory or membrane proteins.

EXAMPLE 1

PREPARATION OF *EIMERIA NECATRIX* AND *EIMERIA TENELLA* OOCYSTS, SPOROCYSTS AND SPOROZOITES

Coccidia. The purified field isolate of *Eimeria necatrix* and *Eimeria tenella* was originally purchased from Dr. Allen Edgar of the University of Auburn. The purity of each isolate was confirmed using oocyst characteristics and histology of infected intestinal tissue. Oocyst size and shape index were within the range of *E. necatrix* and *E. tenella*, respectively.

Lesions were scored by the method of Johnson and Reid (21). The lesions in infected birds were typical of each respective isolate. At 5 days post-infection histological examination revealed larger second generation schizonts in the subepithelium of the mid-intestine (*E. necatrix*) or the ceca (*E. tenella*). Mortality was experienced with *E. tenella* and *E. necatrix* during severe infections (15,000 and 50,000 oocysts respectively). Single oocyst cloning was periodically done to insure purity of each isolate.

Propagation of Oocysts. Pure cultures of each isolate were routinely passaged in 4- to 6-week old SPF white Leghorn chickens. To avoid extraneous coccidial infections, chickens were reared from 1 day of age in plexiglass isolation units. Oocysts were harvested on day 7 post-infection from the ceca using a trypsin-digest method described by Shirley (48). Sporulated oocysts were typically stored at 24° C. in 2% w/v $K_2Cr_2O_7$.

Isolation of Sporocysts. Sporulated oocysts, ($1 \times 10^8$) which had been partially purified from debris by salt floatation, were washed five times in 0.1 M phosphate buffered saline, pH 7.4, (PBS) to remove the potassium dichromate preservative. These oocysts were further cleaned by agitation in a 1.05% sodium hypochlorite solution for 20 minutes followed by five washes in PBS to remove residual sodium hypochlorite and debris. Following the final wash, the cleaned oocysts were resuspended in 10 ml of PBS. Suspended oocysts were then mechanically broken by shaking with an equal volume of glass beads (1.0–1.05 mm). The liberated sporocysts were purified from the oocyst walls and from unbroken oocysts by passage over a glass wool column, centrifuged at 3,000 RPM for ten minutes at 4° C. and resuspended in 10 ml of PBS.

Preparation of Sporozoites. Freshly sporulated oocysts were cleaned by salt floatation, repeated washing and treatment with 1.05% sodium hypochlorite solution. Sporocysts were freed by mechanically breaking oocysts with glass beads (1.0–1.05 mm). To excyst sporozoites, sporocysts were incubated with trypsin and taurodeoxycholic acid (0.25 and 0.50% w/v, respectively) for a period of 1 hour at 41° C. Sporozoites thus obtained were rinsed free of excysting fluid by centrifugation and resuspended in Hank's medium. Fresh Hank's medium was used to dilute sporozoites to the working concentration.

EXAMPLE 2

GENERATION, IDENTIFICATION AND CHARACTERIZATION OF HYBRIDOMAS

Monoclonal antibody. Monoclonal antibodies were derived from hybridomas developed using the method of VanDeusen and Whetstone (56). Briefly, Balb/C ByJ mice were repeatedly immunized with $10^6$–$10^7$ intact *E. tenella* sporozoites. Three days after a final intravenous injection with intact sporozoites, a randomly selected mouse was sacrificed and splenectomized. The splenocytes were separated from fibrous tissue in the organ, and the washed cells fused with the murine plasmacytoma cell line (SP2/OM).

Microneutralization Assay. The microneutralization assay was performed with primary chick kidney cell cultures for *E. tenella* or embryonic porcine lung cells for *E. necatrix*. 1- to 2-week-old chicks were sacrificed and aseptically nephrectomized. The cells were plated into 96-well cultures at a density of approximately $10^4$/well in Earle's LAH medium supplemented with 5% heat-inactivated fetal calf serum. Cultures were maintained at 41° C. in a 5% $CO_2$ atmosphere. When cell cultures reached a level of approximately 50% confluency, 50 microliters of hybridoma test or control sample were added to all wells of the plate. Next, about $3 \times 10^4$ sporozoites suspended in 50 microliters of Earle's culture medium were added to all wells of the plate. Twelve to sixteen hours later, the culture supernatant was replaced with fresh Earle's LAH containing 2% heat inactivated fetal calf serum. The cultures were terminated at 40-44 hours post-infection. Culture supernatant was emptied from the plates at that time. Subsequently, cells were fixed to the plates by the addition of methanol acidified with 5% glacial acetic acid. The fixed cultures were stained with 0.1% toluidine blue before examination. Wells were scored as to the approximate percentage level of inhibition of schizogony; neutralization of parasites by monoclonal antibodies was scored on the basis of the maximum serum dilution still affording complete inhibition of schizont development.

Indirect Fluorescent Antibody Screening. IFA slides were prepared with sporozoites of or *E. tenella* or *E. necatrix* (about $1 \times 10^6$/well). Slides were air dried several hours to overnight before 10 microliters of 1% bovine serum albumin (BSA) was added to each well. Five minutes after adding BSA, 20 microliters of test supernatant was added. Supernatants were incubated at 37° C. for 20 minutes, followed by three rinses with 0.15M PBS with 0.0005% Tween-20 (PBS-Tween). Fluorescein conjugated rabbit anti-mouse antibody (diluted 1:40 in PBS) was added to the samples and allowed to incubate at 37° C. for 20 minutes. The conjugate was rinsed off three times with PBS-Tween before adding mounting medium and cover slip.

Results. Of the several thousand hybridomas developed against *Eimeria tenella*, 24 were found to produce neutralizing antibodies toward the sporozoite stage of the parasite. All of the hybridomas studied produced antibodies that recognized membrane bound antigens, although only the antibody produced by one hybridoma recognized an internal membrane antigen.

In vitro neutralizing potency was compared for several supernatants after the initial cloning of the respective cell lines. Supernatant from certain lines demonstrated the greatest relative propensity for neutralizing sporozoites of *E. tenella*. When antibody content was assessed for each of supernatants tested, it was determined that twenty-fold less of one antibody (designated Ptn 7.2A4/4) was required to neutralize sporozoites than the second most effective neutralizing antibody. Specifically, the amount of Ptn 7.2A4/4 antibody required to neutralize *E. tenella* is approximately $3.5 \times 10^5$ molecules/sporozoite.

The monoclonal antibody designated Ptn 7.2A4/4 has been deposited with the American type Culture Collection in Rockville, Md., U.S.A. 20852, and identified by ATCC accession No. HB8561. This deposit was made pursuant to the provisions of the Budapest Treaty on the International Recognition of the Deposit of Microorganisms.

When the antibody from one cell line identified as Ptn 7.2A4/4 was evaluated with *E. necatrix*, it was observed that a fluorescent staining pattern, similar to that with *E. tenella* had developed. The monoclonal was therefore studied in the in vitro neutralization assay against *E. necatrix*. Said monoclonal antibody was found to possess neutralizing activity against *E. necatrix* at levels within a comparable range observed with a like number of *E. tenella* sporozoites.

EXAMPLE 3

IDENTIFICATION OF THE ANTIGENS OF *E. TENELLA* RECOGNIZED BY NEUTRALIZING MONOCLONAL ANTIBODY Ptn 7.2A4/4

$^{125}$I-Labeling of Eimeria Proteins. A total of $2 \times 10^8$ oocysts from *E. tenella* were processed for iodination. In each case, sporocysts were purified from salt floated, sodium hypochlorite treated oocysts that were broken with glass beads then passed through a glass wool column. Sporocyst membranes were prepared from one-half of the sporocysts by mechanical breakage in 1 ml 10 mM sodium phosphate, 0.15M NaCl, pH 7.2 (PBS) with glass beads in the presence of protease inhibitors: 0.1 mM Phenylmethlysulfonyl fluoride (PMSF), 0.1 mM N-tosyl-L-phenylalanine chloromethyl ketone (TPCK), 1 mM N-alpha-p-tosyl-L-lysine chloromethyl ketone (TLCK) and 10 KIU/ml aprotinin. The remaining sporocysts were treated with trypsin and taurodeoxycholic acid (total volume=1 ml) to excyst sporozoites. Both preparations were pelleted at 45,000 RPM for 45 minutes at 4° C. and resuspended in 1 ml of phosphate buffered saline (PBS). Care was taken to remove all trypsin - deoxycholate residue from the sporozoites by washing with PBS and 1 mM PMSF prior to ultra-centrifugation.

The one ml samples were put into glass scintillation vials which had been coated with 40 micrograms of IODOGEN ™ (1,3,4,6-tetrachloro-3-alpha,6-alpha-diphenylglycouril) solid phase iodination reagent (16,40), dried under nitrogen gas and rinsed with PBS. To each tube, 0.5 mCi of $^{125}$I was added and the samples allowed to incubate for 20 minutes on ice. Afterward, 100 microliters of KI (1 M) was added to each tube to a final concentration of 100 mM, and the reaction was allowed to proceed for an additional 15 minutes on ice. Sporozoite and sporocyst preparations were then diluted to 7 ml with PBS containing 5 mM KI and pelleted at 45,000 RPM for 45 minutes at 4° C.

Extraction of Sporocyst and Sporozoite Membrane Proteins. $^{125}$I labeled sporocyst and sporozoite pellets from the above high speed centrifugation were resuspended in 1 ml of protein extraction buffer (20 mM Tris-HCl, pH 7.5; 50 mM MgCl$_2$; 25 mM NaCl, 1% NP40, 1 mM PMSF, 0.1 mM TPCK, 1 mM TLCK and 10 KIU/ml aprotinin). The suspensions were incubated for 60 minutes on ice with occasional vortexing. Insoluble material was separated from the detergent solubilized protein in a microfuge for 15 minutes at 4° C. The supernatants were stored at $-70°$ C.

TCA Precipitation of $^{125}$I Proteins. Ten microliters of each sample were diluted into 90 microliters of 5 mM KI. Ten microliters of each diluted sample was then added to a solution containing 1 ml of 5% trichloroacetic acid (TCA), 25 microliters BSA (10 mg/ml) and 5 mM KI and incubated on ice for 30 minutes. The precipitated samples were collected by filtration through glass fiber filters, washed twice with 5 ml of 5% TCA, 5 mM KI and three times with 5 ml of 95% ethanol, both at 0° C., and counted in a liquid scintillation counter.

Immunoprecipitation With Monoclonal Antibodies: Fifty microliters of monoclonal antibody were added to 25 microliters of monoclonal antibody dilution buffer (MAB-DIL): 50 mM Tris-HCl, pH 8.6; 150 mM NaCl; 0.1% NP-40; 0.1% BSA, RIA grade; 1 mM TLCK; 1 mM PMSF; 10 KIU/ml aprotinin. Twenty microliters of $^{125}$I labeled protein was then added and the tube vortexed and incubated overnight at 4° C. Rabbit anti-mouse Ig serum (Ig.A, IgG, IgM) was diluted 1:2 in MAB-DIL and 10 microliters added to each immunoprecipitation tube and incubated 1 hour at 4° C. Protein A-Sepharose (10% v/v) was diluted 1:4 in monoclonal antibody wash buffer, (MABW): 50 mM Tris-HCl, pH 8.3; 0.05% NP-40; 0.05% Triton X-100; 150 mM NaCl; 0.02% NaN$_3$; 5 mM KI and 400 microliters added to each tube. The tubes were incubated for one hour at 4° C. with gentle rocking. The immunoprecipitation products were washed twice with cold MABW followed by two room temperature washes with MABW. The pellet was resuspended in 50 microliters of SDS-PAGE sample buffer (25), boiled for 5 minutes and microfuged to remove the protein A-Sepharose. Supernatants were counted and analyzed by SDS-PAGE.

Electrophoretic Transfer of Antigens to Nitrocellulose Paper: Uniodinated sporozoite membrane proteins (detergent solubilized as already described) were separated under either reducing or nonreducing conditions by one dimensional sodium dodecyl sulfate polyacrylamide slab gels and electrophoretically transferred to nitrocellulose paper (55). Electrophoretic blots were processed according to the method of Sharma (46) with the exceptions that sera, monoclonal antibodies and the appropriate conjugates (peroxidase conjugated goat anti-chicken IgG, Kirkegaard and Perry, peroxidase conjugated rabbit anti-mouse IgG (Cappel) were employed for blots of reducing gels, and murine monoclonal antibodies were used in conjunction with the Vectastain TM ABC kit for mouse IgG for nonreducing gels (Vector Labs, Burlington, Calif.). Blots were developed by reacting them with 4-chloro-1-napthol (Sigma; 660 micrograms/ml) and $H_2O_2$ (0.17%) for reduced separation or Vectastain TM reagents for nonreducing separations.

SDS - Polyacrylamide Gel Electrophoresis (SDS-PAGE) of E. tenella Proteins. Total $^{125}I$ labeled sporocyst and sporozoite membrane proteins immunosorbed, and immunoprecipitated proteins were analyzed on, 5-25% exponential or 8-20% linear gradients SDS-polyacrylamide gels at 25 mA. The gels were dried and exposed to Kodak XAR-5 X-ray film overnight at −70° C. Gels used for staining purposes were visualized by Coomassie (15) or silver staining using the manufacturer's labelled instructions (Pierce Chemical).

Results of Immunoprecipitation of E. tenella Antigen with Ptn 7.2A4/4 Mohoclonal Antibody. The surface-labeled E. tenella sporozoite preparation contains two heavily iodinated proteins with apparent molecular weights of 6,500 and 25,000 as judged on reducing SDS-PAGE. The 6,500 dalton protein is readily and specifically immunoprecipitated with monoclonal antibody Ptn 7.2A4/4. Membranes from sporocysts contain two heavily iodinated proteins with apparent molecular weights of 17,000 and 27,000 although several other minor iodinated proteins of various molecular weights are also present. Upon immunoprecipitation of $^{125}I$ labeled sporocyst membrane protein the only antigen precipitated following the reaction with the monoclonal antibody Ptn 7.2A4/4 was the 17,000 dalton protein as determined on reducing SDS-PAGE.

Results of Western Blots of E. tenella Antigens with Ptn 7.2A4/4 Monoclonal Antibody. Under the conditions in which the immunoprecipitated, iodinated polypeptides were analyzed on SDS-PAGE as described above, polyeptides linked by disulfide bonds have been separated. However, reduction of disulfide bonds destroys Ptn 7.2A4/4 reactivity on Western blots in both sporocyst and sporozoite membrane preparations. When iodinated sporocyst and sporozoite membrane preparations were run on SDS-PAGE under non-reducing conditions the major radio labeled species migrates with an apparent molecular weight of 23-25,000. Furthermore, this apparent 23-25,000 dalton species was reactive with monoclonal antibody Ptn 7.2A4/4 by Western blotting. These results suggest that the 17,000 dalton polypeptide and the 8,000 dalton polypeptide are complexed together to form the TA4 antigen. The fact that this other polypeptide component of the TA4 antigen was not observed in immunoprecipitation experiments of iodinated material can be explained by the observation that this other polypeptide does not contain any tyrosines that could be iodinated (see description of the 8,000 dalton polypeptide component of the TA4 antigen in Examples 5 and 9).

EXAMPLE 4

PURIFICATION, IDENTIFICATION AND CHARACTERIZATION OF THE *EIMERIA TENELLA* TA4 ANTIGEN AND FRAGMENTS CONTAINING FRACTIONS THEREOF

Purification of the 17,000 Dalton Peptide Component of the TA4 Antigen. E. tenella sporulated oocysts were resuspended in 10 ml PBS per $10^9$ oocysts and were broken by shaking with an equal volume of glass beads. Membranes were isolated by centrifugation (100,000 xg, 60 min., 4° C.) and the proteins were solubilized in 1% (v/v) NP-40, 10 mM Tris-HCl (pH 7.5), 25 mM NaCl, 1 mM PMSF, 1 mM TLCK, 0.1 mM TPCK and 10 KIU/ml aprotinin. Insoluble material was pelleted with another 100,000×g spin (60 min., 4° C.). The protein was adsorbed to a DEAE-cellulose column equilibriated with 10 mM Tris-HCl (pH 7.7), 0.05% NP-40 and then washed with this buffer containing 50 mM NaCl. After elution with buffer containing 200 mM NaCl, the 17,000 dalton polypeptide was concentrated by acetone precipitation and the precipitate resuspended in loading buffer, boiled and subjected to electrophoresis in SDS-polyacrylamide (15%). Conventional SDS-PAGE sample buffer used in this and other experiments contained 62.5 mM Tris-HCl (pH 6.8), 2% (w/v) sodium dodecyl sulfate, 10% (w/v) glycerol and 0.001% (w/v) bromphenol blue. The buffer also contained 5% (v/v) beta-mercaptoethanol except in experiments in which non-reducing conditions are specified. The 17,000 dalton polypeptide band was identified by staining (Coomassie blue or KCl). The appropriate gel region was excised, the protein electroeluted and concentrated by acetone precipitation. Note that these procedures are denaturing for proteins and peptides bound to each other by disulfide bonds are separated with this method. The 17,000 dalton polypeptide purified by this method was essentially pure.

Purification and Characterization of the TA4 Antigen. As an alternative to purification by gel electrophoresis the sporocyst membrane proteins from the DEAE-cellulose column were dialyzed against 10 mM Tris-HCl, pH8, 0.05% NP-40 and applied to a DEAE-HPLC column (BioRad) equilibrated in this buffer. The column was eluted with a NaCl gradient (0-300mM) in the same buffer. The 17,000 dalton polypeptide (identified by its migration on gel electrophoresis) was found in material eluting at 200 mM NaCl. Fractions containing this protein were applied to a hydroxyapatite column (HPHT-BioRad) equilibrated with 30 mM potassium phosphate, pH 6.5, 0.05% Zwittergent TM 3-12 (Calbiochem-Behring, LaJolla, Calif.) 0.1 mM dithiothreitol. The column was washed with equilibration buffer and developed with a potassium phosphate gradient (0-300 mM) containing 0.05% Zwittergent TM and 0.1 mM dithiothreitol. The 17,000 dalton polypeptide (identified by gel electrophoresis described above) appeared in material eluting at approximately 90 mM potassium phosphate.

Fractions containing the 17,000 dalton polypeptide purified by this method also contained a second peptide of 8,000 daltons. This peptide appears to be linked by a disulfide bridge to the 17,000 dalton polypeptide. If the fractions containing the 17,000 dalton peptide were immunoprecipitated with monoclonal antibody Ptn 7.2A4/4 and the precipitated proteins analyzed by gel electrophoresis under reducing conditions (as above) both the 17,000 and 8,000 dalton polypeptides appear to be immunoprecipitated. Hence, in sporocyst membrane preparations, the 8,000 dalton and 17,000 dalton polypeptides appear to be linked by a disulfide bond (presumably by a cysteine bridge) because the two peptides did not appear on electrophoresis unless a strong reducing agent was present. Under nonreducing conditions, the Ptn 7.2A4/4 reactive species migrates with an apparent molecular weight of 21-24,000.

Preparation of the 11,500 dalton fragment of the TA4 antigen. E. tenella sporocyst membranes were prepared as described above and resuspended in 10 ml of PBS+1% Triton X-100. To this 10 ml membrane suspension was added 10 ml of 80% phenol containing 0.1% 8-hydroxyquinoline. The suspension was then vortexed at maximum speed for three minutes and centrifuged for ten minutes at 4000 RPM. The phenol and the flocculent interface were removed and diluted in five volumes of 100 mM ammonium acetate in methanol and allowed to precipitate at −20° C. overnight. Following two washes in acetone, the insoluble proteins were agitated for 8 hours in 0.5% SDS, and insoluble materials removed by centrifugation at 20,000 RPM for one hour at 4° C. The sample was dialyzed extensively against PBS (pH 7.2) containing AG 501-X8 mixed bed resin (1 gm/500 ml). The 11,500 dalton fragment of the TA4 antigen was then immunoadsorbed from the supernatant using the Ptn 7.2A4/4 monoclonal antibody as follows. This polypeptide was shown to be reactive with the Ptn 7.2A4/4 monoclonal antibody by microtiter plate ELISA.

For microtiter plate ELISA polystyrene 96 well clusters (Immulon II) were sensitized with antigen in 10 mM glycine buffered saline, pH 9.6, incubated overnight at 37° C. The wells were washed with 0.15M PBS with 0.0005% Tween-20, blocked with 3% BSA in PBS-Tween, rewashed, and incubated with Ptn 7.2A4/4 monoclonal antibody diluted in PBS. The wells were washed as before, and then incubated with peroxidase conjugated rabbit anti-mouse IgG serum diluted in PBS. The wells were washed again and then incubated with substrate (2,2'-azino-di-[3-ethyl-benzthiazoline sulfonate]) in the presence of $H_2O_2$. Color development was determined with a Dynatech MR-580 microtiter plate ELISA reader after 15 minutes. The 11,500 dalton fragment of the TA4 antigen was shown to be reactive with the Ptn 7 2A4/4 monoclonal antibody by microtiter plate ELISA.

EXAMPLE 5

AMINO ACID SEQUENCE OF THE 17,000 AND 8,000 DALTON PEPTIDE COMPONENTS OF THE EIMERIA TENELLA TA4 ANTIGEN

Amino Acid Sequence of the 17,000 Dalton Peptide Component of the TA4 Antigen. Amino acid sequencing of the 17,000 dalton peptide was complicated by the finding that the N-terminal amino acid was blocked (i.e. not accessible to Edman degradation (11)). To circumvent this problem the protein was reduced and alkylated and then digested with various chemicals and enzymes. The resulting peptides were purified by reverse phase HPLC (18). The 17,000 dalton polypeptide or the TA4 antigen was digested with CNBr (CN), VB protease (V), chymotrypsin (CH) and Endoprotease Arg-C (R).

Before protease digestion the purified 17,000 dalton polypeptide or the TA4 antigen was treated with 30 mM dithiothreitol, 6M guanidine-HCl (pH 8) for 1 hour at room temperature. Solid iodoacetamide was added to a final concentration of 100 mM, the pH was readjusted to 8 and the sample was incubated for 1 hour at room temperature. Following reduction and alkylation, samples were purified from reagents either by P6DG (BioRad, Richmond, Calif.) spin columns equilibrated in 0.1M MOPS, pH 7.5, 0.1% SDS or by reverse phase HPLC.

For CNBr digestion, the protein sample was treated with 1% CNBr in 70% formic acid for 20 hours at 4° C. The sample was evaporated to dryness in a Savant Speedvac centrifuge and redissolved in 0.1% trifluoroacetic acid (TFA) or 0.1% TFA, 20% acetonitrile (CH CN). V8 digestion was performed in 0.1% SDS, 0.1M MOPS pH 7.5 for 2 hours at room temperature at a ratio of 50 micrograms 17,000 dalton polypeptide: 1 microgram V8. After digestion, the samples were precipitated with 4 volumes of acetone at −20° C. overnight. The acetone precipitates were redissolved as described above. Chymotrypsin digestion was performed in 0.05% Zwittergent ® 3-12, 0.1M $NH_4HCO_3$, pH 7.8 for 1 hour at 37° C. at a ratio of 50:1, 17,000 dalton peptide:chymotrypsin. Samples were acidified with TFA for peptide purification. Arg-C digestion was performed in 0.05% Zwittergent ® 3-12, 0.1M, $NH_4HCO_3$ pH 7.8 for 2 hours at 37° C. at a ratio of 15:1, 17,000 dalton peptide: Arg-C. After acetone precipitation overnight at −20° C., the peptides were mainly in the acetone supernatant. The supernatant was evaporated and the samples redissolved as described above. Peptides were purified on a Vydac C4 column (the Separations Groups, Inc., Hesperia, Calif.) and eluted with a 0-100% $CH_3CN$ gradient in 0.1% TFA.

Amino acid sequencing was performed using a gas phase sequencer (Applied Biosystems, Inc., Foster City, Calif.) according to the procedure of Hunkapiller et al (17). Phenylthiohydantoin (PTH) derivatized amino acids were analyzed by HPLC (5).

The N-terminal amino acid was determined directly by removing the blocking agent. The 17,000 dalton peptide was treated with pyroglutamate aminopeptidase (5:1 protein:PAP) in 0.1M potassium phosphate (pH 8.0), 10 mM EDTA, 5% glycerol, 5 mM dithiothreitol, 0.05% Zwittergent TM 3-12 for 1 hour at 37° C. After treatment, the amino acid sequence could be determined directly suggesting that the N-terminal amino acid glutamine is cyclized to form the blocked residue pyrrolidone carboxylic acid.

The complete amino acid sequence for the 17,000 dalton peptide component of the TA4 antigen is shown in FIG. 1.

Partial Amino Acid Sequence of the 8,000 Dalton Peptide Component of the TA4 Antigen. When the purified 8,000 dalton peptide (derived from the TA4 antigen by reduction and alkylation) was subjected to Edman sequencing the N-terminal amino acid sequence could be determined directly. A partial amino acid sequence of the N-terminal region of the peptide is shown below.

NH$_2$ - ala ala gly thr thr asp ala val ile cys leu thr asn pro ala pro leu glu ala arg ser gln pro phe asp asp glu

EXAMPLE 6

IDENTIFICATION OF THE ANTIGENS OF *E. NECATRIX* RECOGNIZED BY NEUTRALIZING MONOCLONAL ANTIBODY PTN 7.2A4/4

$^{125}$I Labeling of Eimeria Proteins. A total of 2×10$^8$ oocysts from *E. necatrix* were processed for iodination. In each case, sporocysts were purified from salt floated, sodium hypochlorite treated oocysts that were broken with glass beads then passed through a glass wool column. Sporocyst membranes were prepared from one-half of the sporocysts by mechanical breakage in 1 ml PBS with glass beads in the presence of protease inhibitors: 0.1 mM Phenylmethylsulfonyl fluoride (PMSF), 0.1 mM N-tosyl-L-phenylalanine chloromethyl ketone (TPCK), 1 mM N-alpha-p-tosyl-L-lysine chloromethyl ketone (TLCK) and 10 KIU/ml aprotinin. The remaining sporocysts were treated with trypsin and taurodeoxycholic acid (total volume=1 ml) to excyst sporozoites. Both preparations were pelleted at 45,000 RPM for 45 minutes at 4° C. and resuspended in 1 ml of phosphate buffered saline (PBS). Care was taken to remove all trypsin - deoxycholate residue from the sporozoites by washing with PBS and 1 mM PMSF prior to ultra-centrifugation.

The one ml samples were put into glass scintillation vials which had been coated with 40 micrograms of IODO-GEN TM solid phase iodination reagent (16,40), dried under nitrogen gas and rinsed with PBS. To each tube, 0.5 mCi of $^{125}$I was added and the samples allowed to incubate for 20 minutes on ice. Afterward, 100 microliters of KI (1 M) was added to each tube to a final concentration of 100 mM, and the reaction was allowed to proceed for an additional 15 minutes on ice. Sporozoite and sporocyst preparations were then diluted to 7 ml with PBS containing 5 mM KI and pelleted at 45,000 RPM for 45 minutes at 4° C.

Extraction of Sporocyst and Sporozoite Membrane Proteins. $^{125}$I labeled sporocyst and sporozoite pellets from the above high speed centrifugation were resuspended in 1 ml of protein extraction buffer. The suspensions were incubated for 30 minutes on ice with occasional vortexing. Insoluble material was separated from the detergent solubilized protein in a microfuge for 15 minutes at 4° C. The supernatants were stored at −70° C.

TCA Precipitation of $^{125}$I Proteins. Ten microliters of each sample were diluted into 90 microliters of 5 mM KI. Ten microliters of each diluted sample was then added to a solution containing 1 ml of 5% trichloroacetic acid (TCA), 25 microliters BSA (10 mg/ml) and 5 mM KI and incubated on ice for 30 minutes. The precipitated samples were collected by filtration through glass fiber filters, washed twice with 5 ml of 5% TCA, 5 mM KI and three times with 5 ml of 95% ethanol, both at 0° C., and counted, for 10 minutes in a liquid scintillation counter.

Immunoprecipitation With Monoclonal Antibodies: Fifty microliters of monoclonal antibody were added to 25 microliters of MAB-DIL. Twenty microliters of $^{125}$I labeled protein was then added and the tube vortexed and incubated overnight at 4° C. Rabbit anti-mouse Ig serum (IgA, IgG, IgM) was diluted 1:2 in MAB-DIL and 10 microliters added to each immunoprecipitation tube and incubated 1 hour at 4° C. Protein A-Sepharose (10% v/v) diluted 1:4 was added and the tubes were incubated for one hour at 4° C. with gentle rocking. The immunoprecipitation products were washed twice with cold MABW followed by two room temperature washes with MABW. The pellet was resuspended in 50 microliters of SDS-PAGE sample buffer (25), boiled for 5 minutes and microfuged to remove the protein A-Sepharose. Supernatants were assayed for radioactive counts and analyzed by SDS-PAGE.

SDS - Polyacrylamide Gel Electrophoresis (SDS-PAGE) of *E. Necatrix* Proteins. Total $^{125}$I labeled sporocyst and sporozoite membrane proteins immunosorbed, and immunoprecipitated proteins were analyzed on, 5–25% exponential or 8–20% linear gradient SDS-polyacrylamide gels at 25 mA. The gels were dried and exposed to Kodak XAR-5 X-ray film overnight at −70° C. Gels used for staining purposes were visualized by Coomassie (15) or silver staining using the manufacturer's labelled instructions (Pierce Chemical).

Results of Immunoprecipitation of *E. Necatrix* Antigen with Ptn 7.2A4/4 Monoclonal Antibody. The surface-labeled *E. necatrix* sporozoite preparation contains two heavily iodinated proteins with apparent molecular weights of about 6,500 and 25,000 as judged on reducing SDS-PAGE. The 6,500 dalton protein is readily and specifically immunoprecipitated with monoclonal antibody Ptn 7.2A4/4. Membranes from sporocysts contain two heavily iodinated proteins with apparent molecular weights of about 18,000 and 26,000 although several other minor iodinated proteins of various molecular weights are also present. Upon immunoprecipitation of $^{125}$I labeled sporocyst membrane protein the only antigen precipitated following the reaction with the monoclonal antibody Ptn 7.2A4/4 was the 18,000 dalton protein as determined on reducing SDS-PAGE.

EXAMPLE 7

PURIFICATION, IDENTIFICATION AND CHARACTERIZATION OF THE *EIMERIA NECATRIX* NA4 ANTIGEN

Purification and Characterization of the NA4 Antigen. *E. necatrix* sporulated oocysts were resuspended in 10 ml PBS per 10$^9$ oocysts and were broken by shaking with an equal volume of glass beads. Membranes were isolated by centrifugation (100,000×g, 60 min., 4° C.) and the proteins were solubilized in 1% NP-40, 10 mM Tris-HCl (pH 7.5), 25 mM NaCl, 1 mM PMSF, 1 mM TLCK, 0.1 mM TPCK and 10 KIU/ml aprotinin. Insoluble material was pelleted by centrifugation (100,000×g spin, 60 min., 4° C.). The sporocyst membrane proteins were adsorbed to a DEAE-HPLC column (BioRad) equilibrated in 20 mM Tris-HCl, pH 8.1, 0.05% Zwittergent TM 3-12. The column was eluted with a NaCl gradient (0–500 mM) in this buffer containing 0.1 mM dithiothreitol. The NA4 antigen, identified by its migration on gel electrophoresis, was found in material eluting at approximately 275 mM NaCl.

Fractions containing the NA4 antigen were pooled and concentrated using a Centricon TM 10 microconcentrator (Amicon Corp., Danvers, Mass.). The concentrate was diluted with appproximately 10 volumes of 0.01% (w/v) SDS and reconcentrated to lower salt and dithiothreitol levels. The sample was diluted in loading buffer-containing 62.5 mM Tris-HCl (pH 6.8), 2% (w/v) sodium dodecyl sulfate, 10% (w/v) glycerol and 0.001% (w/v) bromphenol blue, boiled and subjected to electrophoresis in 15% SDS-polyacrylamide gels. Under these nonreducing conditions, an approximately 26,000 dalton NA4 antigen was identified by KCl staining (15).

The appropriate region of the gel was excised and the protein was eluted by shaking the gel for 4 hours at room temperature in 1 ml of 10 mM NH$_4$HCO$_3$, 0.02% (w/v) SDS. The NA4 antigen prepared by this method was essentially pure.

When the NA4 antigen was analyzed by SDS-PAGE under reducing conditions (i.e. 5% (v/v) B-mercaptoethanol in the sample buffer) the NA4 antigen appears to contain two polypeptides of 18,000 and approximately 8,000 daltons. In sporocyst membrane preparations, the 18,000 and 8,000 dalton polypeptides therefore appear to be linked by a disulfide bond.

Purification of the *E. Necatrix* Antigen by Immunoadsorption Techniques for In Vivo Testing. Immunoadsorption of *E. necatrix* NA4 antigen was done according to the procedure of Kasper et al with some modifications (22). Briefly, total *E. necatrix* sporocyst membrane, as described earlier in this example was incubated overnight at 4° C. in the presence of Ptn 7.2A4/4 monoclonal antibody. The resultant mixture was then rocked at 4° C. in the presence of goat anti-mouse antisera for two hours followed by reaction with Protein A Sepharose (Sigma; St. Louis, Mo.) under these same conditions. This suspension was poured into a glass column and washed with PBS until base-line adsorbance was achieved in order to remove unbound protein. Nonspecifically bound protein was removed with alternate washes of PBS (pH 8.0) and acetate buffer (0.1M, pH 4.0). Specifically bound antigen was eluted with 60 mM Tris-HCl, pH 6.8 containing 2% SDS. This was followed by subsequent passage of antigen over a Sephadex G-200 column equilibrated and eluted with this same buffer. Sodium dodecyl sulfate was removed by passage over an ExtractiGel D ™ column (Pierce; Rockford, Ill.).

EXAMPLE 8

PARTIAL AMINO ACID SEQUENCE OF THE 18,000 AND 8,000 DALTON PEPTIDE COMPONENTS OF THE *EIMERIA NECATRIX* NA4 ANTIGEN

Amino Acid Sequence of the 18,000 dalton peptide component of the NA4 Antigen. Amino acid sequencing of the 18,000 dalton peptide was complicated by the finding that the N-terminal amino acid was blocked (i.e. not accessible to Edman degradation (11). To circumvent this problem, the NA4 antigen was digested with CNBr and an approximately 16,000 dalton CNBr fragment was purified by reverse phase HPLC (18). For CNBr digestion approximately 10 micrograms of protein was dissolved in 2% CNBr in 70% formic acid overnight at 4° C. The sample was evaporated to dryness in a Savant Speedvac centrifuge and redissolved in 0.1% TFA. The large CNBr fragment was purified on a Vydac C4 column (the Separations Group, Hesperia, Calif.) and eluted with a 0–100% CH$_3$CN:isopropanol 2:1 gradient in 0.1% TFA.

Amino acid sequencing was performed using a gas phase sequencer (Applied Biosystems, Inc., Foster City, Calif.) according to the procedure of Hunkapiller et al (17). Phenylthiohydantoin (PTH) derivatized amino acids were analyzed by HPLC (5). The partial amino acid sequence for the large CNBr fragment is shown below.

NH$_2$—? ? Leu ? Lys Ala Ala Gly Leu Pro Glu Phe Gly Asn Ala Val Gly ? Ala Val Val Leu Pro Ala Tyr Ser

Partial Amino Acid Sequence of the 8,000 Dalton Peptide Component of the NA4 Antigen. The N-terminal amino acid sequence of the 8,000 dalton peptide component of the NA4 antigen could be determined directly by sequencing the NA4 antigen. The purified NA4 antigen eluted from the SDS-PAGE gel was concentrated approximately 6-fold using a Centricon ™ 10 microconcentrator. To remove glycine in the sample that was eluted from the SDS gel 20 volumes of water was added twice to the concentrate and the sample was then reconcentrated. The concentrated sample was applied directly to the sequenator. A partial amino acid sequence of the N-terminal region of the peptide is shown below:

NH$_2$—Ala Ala? Thr? Asp Ala Val Ile Cys Leu Thr Asn Pro Ala Pro Leu Ala Ala Gly Ser Pro Pro ? Phe ? Asp Glu ? Trp

EXAMPLE 9

ISOLATION AND CHARACTERIZATION OF A GENOMIC DNA CLONE ENCODING THE *EIMERIA TENELLA* TA4 ANTIGEN

Isolation of DNA from *E. tenella* Sporulated Oocysts. Sporulated oocysts (5×10$^8$) were washed and sporocysts were isolated as described previously. Isolated sporocysts were washed 2× with 0.1M Tris-HCL, (pH 8.5), 0.2M NaCl, 10 mM EDTA,. Sporocysts were lysed by incubation for 30 min. at 65° C. in 0.1M Tris-HCl, (pH 8.5), 0.2M NaCl, 50 mM EDTA, 1% SDS, 150 micrograms/ml Proteinase K. After cooling to room temperature the DNA was gently extracted with an equal volume of liquified phenol for 1 hour. After centrifugation for 10 min. at 3,000 rpm, the aqueous layer was removed and the interface and phenol were re-extracted with 10 mM Tris-HCl (pH 8), 1 mM EDTA. The aqueous phases were pooled and extracted 1× with phenol and 2× with chloroform: isoamyl alcohol (24:1). DNA was isolated by ethanol precipitation. The DNA pellet was redissolved in 10 mM Tris-HCl (pH 8), 1 mM EDTA and treated with 0.15 mg/ml DNase free-RNase A for 1 hour at 37° C. After RNase digestion, the sample was extracted 1× with phenol, 1× with chloroform: isoamyl alcohol and then precipitated with ethanol. On agarose gels, the size of the DNA was determined to be greater than 20 kilobase pairs.

Construction of the *E. tenella* Genomic Library in Bacteriophage λgt wes λB. The *E. tenella* genomic DNA library in bacteriophage λgt wes λB (26) was constructed using methods described by Maniatis et al. (33). Phage were purified by polyethyleneglycol precipitation, chloroform extraction and CsCl gradient centrifugation. Purified phage were disrupted with 1% SDS, 50 mM EDTA and 150 micrograms/ml Proteinase K, and DNA was purified by phenol extraction, chloroform extraction and ethanol precipitation. The *E. tenella* genomic DNA and phage DNA were digested to completion with EcoRI. The left and right arms of the phage DNA were annealed at their cohesive ends and the arms were purified by sucrose density gradient centrifugation. 30 micrograms of EcoRI digested DNA arms were ligated to 6 micrograms of EcoRI digested *E. tenella* DNA using T4 DNA ligase. 20 micrograms of the ligated DNA were packaged in vitro into phage particles producing a library of 5×10⁶ recombinant phage particles.

Synthetic Oligonucleotides. Oligonucleotide probes complementary to regions of the gene encoding the 17,000 dalton peptide component of the TA4 antigen were synthesized using a Biosearch Sam I (Biosearch, Inc., San Rafael, Calif.). The expected DNA sequences of the appropriate regions were deduced from the amino acid sequence of the 17,000 dalton peptide. Because of the ambiguity in the genetic code, the exact DNA sequence cannot be predicted. "Mixed probes" were designed and synthesized which contained a mixture of DNA sequences, one of which should have perfect match homology with the gene for the 17,000 dalton peptide.

Oligonucleotide COD 92 was based on amino acids 6 to 12 of peptide V1 (see Example 5 for amino acid sequence of the 17,000 dalton peptide). It contained a mixture of 256 different sequences. The structure of oligonucleotide COD 92 is:

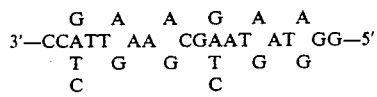

Amino Acid Sequence: Gly Asn Phe Ala Tyr Tyr Pro

Oligonucleotide COD 94 was based on amino acids 3 to 8 of peptide V2 of the 17,000 dalton peptide. It contained a mixture of 64 different sequences:

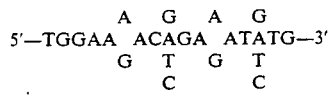

Amino Acid Sequence: Trp Lys Thr Glu Ile Cys

Oligonucleotide COD 108 was based on amino acids 25–30 of peptide V1. It contained a mixture of 16 different sequences. The structure of oligonucleotide COD-108 is:

Amino Acid Sequence: Glu Tyr Trp Lys Gly Gly

Screening the *E. tenella* Genomic DNA Library. Recombinant phage of the *E. tenella* genomic DNA library were plated on 15 cm plates at high density, up to 2–3×10⁴ phage per plate. Nitrocellulose filter replicas of each plate were prepared according to the method of Benton and Davis (2). The filters were then incubated with the appropriate synthetic oligonucleotides which had been labeled to high specific activity with (³²P)-dATP and T4 polynucleotide kinase. Positive plaques were identified by autoradiography. Only those plaques that hybridized to both oligonucleotides COD-92 and 108 were scored positive.

Small blocks of agar were cut from the plates in regions that corresponded to the region of the filter containing the hybridizing DNA. The phage were eluted, replated at lower density (20-100/plate) and rescreened with all three oligonucleotide probes. Pure isolated positive plaques or clones were picked. Phage 108-1 hybridized strongly to oligonucleotide COD-92 and moderately to oligonucleotides COD-108 and 94. Phage 108-1 was grown up on a larger scale for purification and characterization of the *E. tenella* DNA insert. Characterization of phage 108-1 DNA showed an EcoRI insert of 5,500 bp.

Detailed Characterization of the Genomic Clone Encoding the 17,000 Dalton Peptide - Restriction Map. The 5,500 bp EcoRI fragment insert of clone 108-1 was subcloned from the phage vector into plasmid pUC 9 (57). The recombinant plasmids were digested with a variety of restriction endonucleases to determine the position of key restriction sites in the genomic DNA clone. The position of restriction sites within the DNA was needed to determine the location and orientation of the 17,000 dalton peptide gene and to develop a strategy to sequence the EcoRI genomic DNA fragment. The restriction map is presented in FIG. 2. The location and orientation of the gene for the 17,000 dalton peptide is shown on this map.

DNA Sequence Analysis of Clone 108-1. The BglII-EcoRI fragment of clone 108-1 containing the gene for the 17,000 dalton peptide component of the TA4 antigen was sequenced by the dideoxy method of Sanger (45) using various restriction enzyme fragments. Primers for DNA synthesis included oligonucleotides COD-92, 94 and 108 as well as other synthetic oligonucleotides. The DNA sequence is shown in FIG. 3.

Structure of the Gene Encoding the TA4 Antigen. The DNA sequence agrees with that predicted by the amino acid sequence analysis. In addition, there are three features of the gene which are not apparent from the protein sequence. Using protein sequence information and general information regarding the structure of secretory proteins, the structure of the gene for the TA4 antigen has been deduced.

From the known amino terminus of the sporocyst membrane 17,000 dalton peptide (see Example 5), Gln-Asp-Tyr---, it is apparent that the gene encodes an extra 23 amino acids upstream. This DNA sequence is a typical "signal" sequence found at the amino terminus of genes for many secretory or membrane proteins (3, 24). The peptide it encodes is required for the export of proteins from their site of synthesis (the cytoplasm) to and/or through the plasma membrane. The signal peptide is usually removed during the secretory process. It is not surprising that the TA4 antigen is made with a signal peptide since it most likely traverses the cytoplasmic membrane in order to be found at the outer surface of the sporozoite. The amino terminus of the signal sequence is assumed to be the Met codon since, essentially, synthesis of all proteins begin with methionine.

There are three regions of the gene in which the DNA sequences do not coincide with the protein sequence. The first is a 101 bp segment occurring within the codon for Val-7 of the known mature 17,000 dalton protein sequence. The second is a 114 bp sequence between the codons for Gly-65 and Gly-66 of the 17,000 dalton peptide. The third is a 124 bp sequence within the codon for Asp-186 of the 8,000 dalton peptide. These three sequences are intron structures typically found within the coding regions of many eukaryotic genes. They are present in the precursor to the mRNA, and then removed by an RNA recombination mechanism known as "splicing," to give the mature mRNA an uninterrupted coding sequence. The DNA sequences around the "splice junctions" are consistent with those seen in other eukaryotic genes (47).

The sequence of the 17,000 dalton peptide appears to terminate with the sequence Gly-Gly corresponding to codons 157 and 158. We have also identified an 8,000 dalton peptide with the sequence beginning with Ala-162 extending to Glu-188. The peptide sequence Arg-Arg-Leu corresponding to codons 159 through 161 has not been found. It is probable that this tripeptide is removed by a mechanism similar to the cleavage of other proteins such as insulin (53). Hence the two peptides of the TA4 antigen are encoded by a contiguous nucleotide sequence, and at least one proteolytic step occurs to generate the 8,000 dalton peptide beginning with Ala-162.

EXAMPLE 10

ISOLATION AND CHARACTERIZATION OF A GENOMIC DNA CLONE ENCODING THE *EIMERIA NECATRIX* NA4 ANTIGEN

Isolation of DNA from *E. Necatrix* Sporulated Oocysts. Sporulated oocysts ($5 \times 10^8$) were washed and DNA from sporocysts was isolated as described in Example 9.

Construction of the *E. Necatrix* Genomic Library in Bacteriophage λgt wes λB. The *E. necatrix* genomic DNA library in bacteriophage λgt wes λB (26) was constructed as described in Example 9. 15 micrograms of EcoRI digested DNA arms were ligated to 3 micrograms of EcoRI digested *E. necatrix* DNA using T4 DNA ligase. 1 microgram of the ligated DNA was packaged in vitro into phage particles producing a library of $2 \times 10^6$ recombinant phage particles.

Screening the *E. necatrix* Genomic DNA Library. Nitrocellulose filter replicates of recombinant phage of the *E. necatrix* genomic DNA library were screened with the 785 base pair Sac I - Pvu II fragment of the *E. tenella* genomic clone 108-1-2 which had been nick translated with [$^{32}$P]-dATP. Positive plaques that hybridized to the nick-translated probe were picked, plaque purified and DNA was prepared as described previously. Positive phage 7 was grown up on a larger scale for purification and characterization of the *E. necatrix* DNA insert.

Detailed Characterization of the Genomic Clone Encoding the 18,000 Dalton Peptide - Restriction Map. The 3,900 bp EcoRI fragment insert of clone 7 was subcloned from the phage vector into plasmid pUC9 (57) to produce clone 7-49. This recombinant plasmid was digested with a variety of restriction endonucleases to determine the position of key restriction sites in the genomic DNA clone. The position of restriction sites within the DNA was needed to determine the location and orientation of the 18,000 dalton peptide gene and to develop a strategy to sequence the EcoRI genomic DNA fragment. The restriction map is presented in FIG. 4. The location and orientation of the gene for the 18,000 dalton peptide is shown on this map.

DNA Sequence Analysis of Subclone 7-49. The fragment of clone 7-49 containing the gene for the 18,000 dalton peptide component of the *E. necatrix* NA4 antigen was sequenced by the dideoxy method of Sanger (45) using various restriction enzyme fragments. Primers for DNA synthesis included oligonucleotides COD 92, 94 and 108 as well as other synthetic oligonucleotides. The DNA sequence is shown in FIG. 5.

Structure of the Gene Encoding the *E. necatrix* NA4 Antigen. The DNA sequence agrees with that predicted by the partial amino acid analysis.

Based on polyacrylamide gel electrophoresis under non-reducing conditions both the *E. necatrix* and *E. tenella* antigens have an apparent molecular weight of 25-26,000. Electrophoresis under reducing conditions has shown that both antigens are composed of two polypeptides linked by a disulfide bond. Comparison of the *E. necatrix* gene to the *E. tenella* gene suggests the gene structure is similar to the *E. tenella* gene in the three features discussed previously, namely: (1) the gene encodes a 23 amino acid signal peptide; (2) there are three introns within the gene and (3) the gene encodes a 26,000 dalton peptide which has the same proteolytic processing site (Arg-Arg-Leu) to produce 18,000 and 8,000 dalton peptides.

From analysis of the DNA sequence of the *E. necatrix* gene compared to the *E. tenella* gene, similarities and differences between the two proteins can be inferred. FIG. 6 shows the alignment of the *E. tenella* and *E. necatrix* genes and the predicted amino acid sequences. The 3 intron entrance/exit sites are preserved in both genes. The two A4 antigen proteins show 86% homology in their amino acid sequences. All cysteine amino acid residues and presumably disulfide bonds are preserved. The *E. necatrix* protein shows an insertion of one amino acid between positions 2 and 3 of the mature 17,000 daton polypeptide of the *E. tenella* protein. In addition, the *E. necatrix* protein lacks the serine residue that is at position 45 in the *E. tenella* protein and the amino acids corresponding to positions 223 to 228 in the mature *E. tenella* protein.

FIG. 7 shows the alignment of the three introns within the genes. Intron A is 101 bp in both species and shows 89% sequence homology. Intron B is 114 bp in *E. tenella* and 122 bp in *E. necatrix* with 74% homology. Intron C is 124 bp in *E. necatrix* and 117 bp in *E. necatrix* with 77% sequence homology. Thus, the introns are clearly different.

EXAMPLE 11

USE OF *E. TENELLA* TA4 ANTIGEN AND AN 11,500 DALTON FRAGMENT THEREOF TO ELICIT SPOROZOITE NEUTRALIZING SERUM RESPONSE AND PROTECTIVE RESPONSE AGAINST *E. TENELLA* IN CHICKENS

Eliciting Sporozoite Neutralizing Serum Response Against *E. tenella* Using the TA4 Antigen. The TA4 antigen used in these experiments was prepared from sporocysts by methods described in Example 4 for the preparation of the nonreduced intact TA4 antigen. Purity and identity of the protein was confirmed by SDS-PAGE and immunoreactivity with monoclonal antibody Ptn 7.2A4/4 prior to use in chickens.

Vaccine preparations were formulated at a level of one volume antigen to three volumes of oil carrier consisting of about 5% Arlacel A, 94% Drakeol 6-VR, 1% Tween 80 so that each 0.1 ml dose contained approximately 15 micrograms of TA4 antigen. When necessary, antigen was diluted with PBS (pH7.2) to the level desired for formulation. Chickens received 0.1 ml dose by intramuscular route in the neck muscle. Antigen was administered two more times by the same route using the same amount at two-week intervals.

Three days prior to each administration of protein, and eleven days after the final administration, birds were bled for collection of serum samples. Heat inactivated sera were tested independently in the sporozoite microneutralization assay as described in Example 2.

Neutralization of parasites by serum was scored on the basis of the maximum serum dilution affording 50% inhibition of schizont development.

The results as set forth below indicate that whereas nonvaccinated birds receiving carrier only had no demonstrable neutralizing antiserum titers against *E. tenella* sporozoites, birds receiving three doses of the antigen had demonstrable neutralizing antiserum titers.

| TA4 Antigen Induced Sporozoite Neutralization Assay Data | | | |
|---|---|---|---|
| | Sporozoite Neutralization Titers (ND50%)$^d$ | | |
| Serum Samples | Highest | Lowest | Median Titer |
| Prebleed$^a$ | N.D.$^b$ | N.D. | N.D. |
| Nonvaccinate Controls (n = 9) | N.D. | N.D. | N.D. |
| Carrier Only (n = 14) | N.D. | N.D. | N.D. |
| Carrier/Protein Vaccine (n = 15) | 1:32 | N.D. | 1:8 |
| Immune serum$^c$ (Whole Sporozoite Vaccinates) | — | — | 1:32 |

$^a$Serums from birds within each treatment group were pooled and tested.
$^b$N.D. = No detectable neutralization
$^c$Pooled serum from several birds
$^d$50% neutralization dose Eliciting a Protective Response in Chickens Using the TA4 Antigen. Sixty-three (59) days after the final vaccination, some birds were challenged, orally with 1,000 sporulated *E. tenella* oocysts. This was followed the next day with 3,000 sporulated *E. tenella* oocysts also given orally. Caecal lesions were scored 5 days after the final challenge. The results are tabulated below.

| Protection of TA4 Antigen Vaccinated Birds Against *E. tenella* Coccidiosis | |
|---|---|
| | Lesion Score $\overline{X} \pm$ S.D. |
| Nonvaccinate Controls (n = 17) | 3.4 ± 0.6 |
| Adjuvant Only (n = 5) | 4.0 ± 0.0 |
| TA4 Antigen/Adjuvant Vaccinates (n = 8) | 2.4 + 1.3 |

Eliciting Sporozoite Neutralizing Serum Response Against *E. tenella* Using the TA4 Antigen. The immunogen used in these experiments was prepared from sporocysts by phenol extraction as described in Example 4. Purity and identity of the protein was confirmed by SDS-PAGE and immunoreactivity with monoclonal antibody Ptn 7.2A4/4 prior to use in chickens.

Lyophilized purified antigen was dissolved in 0.15 M phosphate buffered saline and emulsified in three parts carrier consisting of about 5% Arlacel A, 94% Drakeol 6-VR, 1% Tween-20 at a final antigen concentration of 70 micrograms/ml. Chickens received about 14 micrograms protein/0.2 cc dose by intramuscular route in the neck muscle. Antigen was again administered two weeks later by the same route using the same amount.

One day prior to each administration of protein, and two weeks after the second administration of protein, birds were bled for collection of serum samples. Heat inactivated sera were tested independently in the sporozoite microneutralization assay as described in Example 2.

The results as set forth below indicate that whereas nonvaccinated birds receiving carrier only had no demonstrable neutralizing antiserum titers against *E. tenella* sporozoites, birds receiving two doses of antigen had demonstrable neutralizing antiserum titers of up to 1:81.

| Sporozoite Neutralizing Assay Data | | | | |
|---|---|---|---|---|
| | | Sporozoite Neutralization Titers (ND50%)$^a$ | | |
| Serum Sample* | Bleeding | Highest | Lowest | Median Titers |
| Prebleed | 0 Week | 1:3 | 1:3 | 1:3 |
| Nonvaccinate Controls | 2 Weeks | 1:3 | 1:3 | 1:3 |
| | 4 Weeks | 1:3 | 1:3 | 1:3 |
| Carriers only | 2 Weeks | 1:3 | 1:3 | 1:3 |
| | 4 Weeks | 1:3 | 1:3 | 1:3 |
| Carrier/Protein Vaccine | 2 Weeks | 1:3 | 1:3 | 1:3 |
| | 4 Weeks | 1:81 | 1:3 | 1:9 |
| Immune Serum** (Whole Sporozoite vaccine) | — | — | — | 1:81 |

*5 birds per group
**Pooled serum from several birds
$^a$A 50% neutralizing dose Eliciting a Protective Response in Chickens Using the 11,500 Dalton Fragment of the TA4-Antigen. Birds received approximately 3 micrograms of antigen in the aforementioned carrier one time in the neck muscle. A second group of birds received the carrier substance only. A final group of nonvaccinate (sentinel) birds were housed with each of the two aforementioned groups. Birds were exposed to coccidia by being housed in *E. tenella* contaminated cages. Approximately two weeks later, the birds were examined and found to have been infected by *E. tenella*. The following observations were noted.

| Protection of Vaccinate Birds Against Coccidiosis by *E. Tenella* | | |
|---|---|---|
| Treatment | Lesion Score $\overline{X} \pm$ S.D. | No. of Deaths |
| Adjuvant only (n = 5) | 3.8 ± 0.4 | 2 |
| Antigen vaccination (n = 5) | 1.0 ± 0.8 | 0 |
| Sentinal Birds (n = 6) | 4.0 ± 0.0 | 6 |

Because the conditions described above closely mimic the natural means of exposure to *E. tenella* in the field, the data presented show clear evidence of the usefulness of the invention for protection against coccidiosis due to *E. tenella*.

Demonstration that Neutralizing Serum Antibodies of Chickens Recognize the 17,000 Dalton Polypeptide Component of the TA4 Antigen. Analysis of serum antibody specificity for the 17,000 dalton polypeptide component of the TA4 antigen was performed using Western blots (4,46). All chicken sera with demonstrable neutralization titers to *E. tenella* sporozoites were shown to possess immunoglobulins with specificity for the 17,000 dalton peptide component of the TA4 antigen; conversely, no sera from nonresponding or control birds had specificity for the 17,000 dalton polypeptide or any other sporozoite protein.

Demonstration that Neutralization Serum Antibodies of Chicken Compete With Monoclonal Antibody Ptn 7.2A4/4. Sera from vaccinated birds with demonstrable neutralization titers to *E. tenella* sporozoites, as well as corresponding control sera were tested for the ability to compete with antibody Ptn 7.2A4/4 for binding sites on sporozoite membranes. Polystyrene 96 well clusters (Immulon II) were sensitized with 50 microliters of sporozoite membrane proteins in 10 mM glycine buffered saline, pH 9.6, at a level of approximately 100 micrograms total protein/ml. Serial two-fold dilutions of sera were prepared in 0.15M phosphate buffered saline with 0.0005% Tween-20 containing a 1:80 dilution of alkaline phosphatase conjugated to Ptn 7.2A4/4 and then transferred to the sensitized plates at a final volume of 75 microliters/well. After incubation at 37° C. for 30 minutes, the plates were rinsed free of unreacted materials using PBS-Tw. Afterward, substrate consisting of the sodium salt of P-phosphonitrophenol dissolved in 1M diethanolamine buffer at a level of 1 mg/ml was added to each well of the plate to a final volume of 100 microliters. The resultant reaction product was monitored spectrophotometrically. From the study, it was possible to ascertain that sera from birds responding to the vaccination as evidenced by neutralization and immunoblots also contained antibody which competed with monoclonal antibody Ptn 7.2A4/4. This experiment provides direct evidence that antigen purified from sporozoite membranes by either immunoaffinity chromatography using monoclonal Ptn 7.2A4/4 or conventional chromatography is capable of stimulating an immune response in chickens to the epitope defined by monoclonal Ptn 7.2A4/4.

EXAMPLE 12

USE OF E. TENELLA PROTEIN TO ELICIT SPOROZOITE NEUTRALIZING SERUM RESPONSE AGAINST E. NECATRIX IN CHICKENS

Heat inactivated sera from birds vaccinated with the 11,500 dalton containing preparation of the E. tenella TA4 antigen (Example 4) were pooled and tested in the neutralization assay (Example 2) substituting embryonic porcine lung cells. The results are as listed in the following table.

| Treatment | Neutralization Titer |
| --- | --- |
| Non-immune chicken serum | 1:6 |
| TA4 Antigen Vaccination | 1:24 |
| E. tenella whole sporozoite immune serum | 1:48 |

The data demonstrate the development of an elevated serum neutralization titer against E. necatrix when birds receive the purified 11,500 dalton fragment of the TA4 antigen. Because it has been previously demonstrated that administration of the TA4 antigen results in the elevation of serum neutralizing titers to E. tenella, and that administration of the TA4 antigen results in protection from E. tenella challenge, and since E. necatrix sporozoite neutralization titers are elevated by the administration of TA4 antigen, one skilled in the art would predict that protection against E. necatrix challenge will also result from administration of the TA4 antigen.

EXAMPLE 13

USE OF PURIFIED E. NECATRIX NA4 PROTEIN TO ELICIT A SPOROZOITE NEUTRALIZING SERUM RESPONSE AGAINST E. TENELLA IN CHICKENS

The antigen used in these experiments was prepared from sporocysts as described in Example 7. Prior to use in chickens, identity and purity of the protein was confirmed by SDS-PAGE and immunoreactivity with monoclonal antibody Ptn 7.2A4/4.

One part purified antigen diluted in 0.15M phosphate buffered saline was emulsified to a final volume of one ml in three parts carrier consisting of about 5% Arlacel A, 94% Drakeol 6-VR, 1% Tween-20. Chickens received 15 micrograms antigen/0.2cc dose in the neck. Antigen was administered at 14-day intervals two additional times by the same route.

Three days prior to each administration of protein, and eleven days after the final administration, birds were bled for collection of serum samples. Heat inactivated sera were tested independently in the sporozoite microneutralization assay as described in Example 2.

The results as set forth below indicate that whereas nonvaccinated birds receiving carrier only had no demonstrable neutralizing antiserum titers against E. tenella sporozoites, birds receiving three doses of the antigen had demonstrable neutralizing antiserum titers.

| | NA4 Antigen Induced Sporozoite Neutralization Assay Data | | |
| --- | --- | --- | --- |
| | Sporozoite Neutralization Titers (ND50%)[c] | | |
| Serum Sample | Highest | Lowest | Median Titer |
| Prebleed[a] | 1:2 | 1:2 | 1:2 |
| Nonvaccinate Controls (n = 9) | 1:2 | 1:2 | 1:2 |
| Carrier Only (n = 14) | 1:4 | 1:2 | 1:2 |
| Carrier/NA4 Protein Vaccine (n = 15) | 1:32 | 1:2 | 1:8 |
| Immune Serum[b] (Whole Sporozoite Vaccinates) | — | — | 1:32 |

[a]Serums from birds within each treatment group were pooled and tested.
[b]Pooled serum from several birds.
[c]50% neutralization dose

EXAMPLE 14

USE OF PURIFIED E. NECATRIX NA4 PROTEIN TO ELICIT A PROTECTIVE RESPONSE TO AN E. TENELLA CHALLENGE

On three occasions at 14-day intervals, 4 week-old white Leghorn chickens received 15 micrograms of immunoaffinity purified NA4 protein/0.2cc dose by intramuscular route in the neck muscle. The antigen was formulated in PBS and emulsified 60 micrograms/ml final volume in three parts of the aforementioned carrier. A second group of birds received the carrier substrate only. A third group was not vaccinated. A final group of nonvaccinated birds housed with the NA4 vaccinated birds served as sentinels. Birds were randomly placed in an E. tenella contaminated battery. Ten days after exposure to E. tenella, birds were challenged with an oral dose of $1 \times 10^4$ E. tenella oocysts. Twenty-four hours later, birds received an additional $3 \times 10^4$ oocysts orally. All birds were sacrificed and lesions scored 5 days after receiving the last oral dose of E. tenella.

| Treatment Groups | Lesions Scores ($\overline{X} \pm$ S.D.) |
| --- | --- |
| Carrier Only | 4.0 ± 0.0 |
| Carrier/Protein | 2.4 ± 1.3 |
| Nonvaccinated Controls | 3.4 ± 0.6 |

These results would suggest to one skilled in the art that the birds receiving NA4 protein were measurably protected against disease due to severe challenge with *E. tenella*. The lesion scores for groups receiving the NA4 protein were lower than respective control groups.

EXAMPLE 15

FORMULATION AND USE OF ANTIGEN FOR PROTECTION OF CHICKENS AGAINST DISEASE CAUSED BY *E. NECATRIX*

A composition for immunization of chickens against coccidiosis caused by *E. necatrix* may be prepared from the intact NA4 antigen or fragments identified by monoclonal antibody Ptn 7.2A4/4. As example, one suitable carrier for the antigen is about 5% Arlacel A, 94% Drakeol 6-VR, 1% Tween-20. The vaccine may be prepared by formulating one part of an aqueous solution of the antigen with 3 parts Arlacel A/Drakeol 6-VR/Tween 20 to a final concentration of about 10 micrograms antigen/dose. The vaccine may be administered to chickens of any age by the intramuscular route. Properly vaccinated birds would be protected against disease, depressed performance or death caused by field challenge with *E. necatrix*.

EXAMPLE 16

FORMULATION AND USE OF ANTIGEN FOR PROTECTION OF CHICKENS AGAINST DISEASE CAUSED BY *E. TENELLA*

One composition may include that described in Example 15. The vaccine may be administered to chickens of any age by the intramuscular route. Properly vaccinated birds would be protected against disease, depressed performance or death caused by field challenge with *E. tenella*.

References

1. Ali, N. S., Binnerts, W. T. and Klimes, B. (1972). Immunization by (sic) irradiated *Eimeria acervulina*. J. Prot. 19, 177.
2. Benton, W. D. and Davis, R. W. (1977). Screening λgt recombinant clones by hybridization to single plaques in situ. Science 196, 180–182.
3. Blobel, G. and Dobberstein, B. (1975). Transfer of proteins across membranes I. Presence of proteolytically processed and unprocessed nascent immunoglobulin light chains on membrane-bound ribosome of murine myeloma. J. Cell Biol. 67, 835–851.
4. Burnette, W. M. (1981). "Western Blotting": Electrophoretic transfer of proteins from sodium dodecyl sulfate - polyacrylamide gels to unmodified nitro-cellulose and radiographic detection with antibody and radioiodinated protein A. Anal. Biochem. 112, 195.
5. Cohen, S. A., Tarvin, T. L. and Bidlingmeyer, B. A. (1984). Analysis of amino acids using precolumn derivatization with phenylisothiocyanate. American Laboratory 16, 48–59.
6. Danforth, H. D. (1982). Development of hybridoma-produced antibodies directed against *Eimeria tenella* and *E. mitis*. J. Parasitol. 68, 392.
7. Danforth, H. D. (1982). Use of monoclonal antibodies directed against *Eimeria tenella* sporozoites to determine stage specificity and in vitro effect on parasite penetration and development. Am. J. Vet. Res. 44, 1722.
8. Danforth, H. D. and Augustine P. C. (1983). Specificity and cross-reactivity of immune serum and hybridoma antibodies to various species of avian coccicia. Poultry Science 62, 2145.
9. Davis, P. J., Parry, S. H. and Porter, P. (1978). The role of secretory IgA in anti-coccidial immunity in the chicken. Immunology 34, 879.
10. Davis, P. J. and Porter, P. (1979). A mechanism for secretory IgA mediated inhibition of the cell penetration and intracellular development of *Eimeria tenella*. Immunology 36, 471.
11. Edman, P. and Begg, G. (1967). A protein sequenator. Automated Equipment for Sequence determination, Eur. J. Biochem 1, 80.
12. Giambrone, J. J., Klesius, P. H. and Edgar S. A. (1980). Avian Coccidiosis: Evidence for a cell-mediated immune response. Poultry Sci. 59, 38.
13. Gibbons, R. A., Sellwood, R., Burrow, M. and Hunter, P. A. (1977). Inheritance of resistance to neonatal *E. coli* diarrhea in the pig: Examination of the genetic system. Theor. Appl. Genet. 51, 65.
14. Gore, T. C., Long, P. L., Kogut, M. and Johnson, J. (1983). Attenuation of *Eimeria necatrix* and *E. tenella* of U.S. origin by serial embryo passage. Avian Disease 27, 569.
15. Hagar, D. A. and Burgess, R. R. (1980). Elution of proteins from sodium dodecyl sulfate - polyacrylamide gels, removal of sodium dodecyl sulfate, and renaturation of enzymatic activity: Results with Sigma units of *Escherichia coli* RNA polymerase, heat germ topoisomerase, and other enzymes. Anal. Biochem. 109:76.
16. Howard, R. J., Koushal, D. C. and Caster, R. (1982). Radio-iodination of parasite antigen with 1,3,4,6-tetrachloro-3,alpha-6,alpha-diphenyl glycouril (IODOGEN ™ ) Studies with zygotes of *Plasmodium gallinarum*. J. Protozol. 29:114.
17. Hunkapiller, M. W., Hewick, R. M., Dreyer, W. J. and Hood, L. E. (1983). High sensitivity sequencing with a gas phase sequenator. Methods in Enzymology 91, Academic Press, New York, 399–413.
18. Hunkapiller, M. W., Strickler, J. E. and Wilson, K. J. (1984). Contemporary Methodology for Protein Structure Determination. Science 226, 304–311.
19. Jeffers, T. K. (1975). Attenuation of *Eimeria tenella* through selection for precociousness. J. Parasitol. 61, 1083.
20. Jeffers, T. K. (1976). Genetic recombination of precociousness and anticoccidial drug resistance on *Eimeria tenella*. Zeitschrift fur Parasitenkunde 50, 251.
21. Johnson, J. and Reid, W. M. (1970). Anticoccidial Drugs: Lesion scoring techniques in battery and floor pen experiments with chickens. Exp. Parasitology 38, 36.
22. Kasper, L. H., Crabb, J. H., and Pfefferkorn, E. R. (1983). Purification of a major membrane protein of *Toxoplama gondii* by immunoabsorption with a monoclonal antibody. J. Immunol. 130, 2407.
23. Keusch, G. T. (1979). Specific membrane receptors: Pathogenic and therapeutic implications in infectious diseases. Rev. Inf. Dis. 1, 517.
24. Kriel, G. (1981). Transport of proteins across membranes. Ann. Rev. Biochem. 50, 317–348.
25. Laemmli, U. K. (1970). Cleavage of structural proteins during the assembly of the head of bacteriophage T4, Nature 227, 680.
26. Leder, P., Tiemeier, D. and Enquist, L. (1977). EK2 derivatives of bacteriophage lambda useful in cloning of DNA from higher organisms: the λgt wes system. Science 196, 175–177.
27. Long, P. L. (1972) *Eimeria mivti*: Reproduction, pathogenicity and immunogenicity of a strain maintained in chick embryos by serial passage. J. Comp. Pathol. 82, 839.
28. Long, P. L. (1974). Further studies on the pathogenicity and immunogenicity of an embryo adapted strain of *Eimeria tenella*. Avian Pathology 3, 255.
29. Long, P. L. (1982). *The Biology of the Coccidia*. University Park Press, Baltimore. Pg. 44.
30. Long, P. L., Johnson, J., and Gore, T. C. (1982). Attenuation of a strain of *Eimeria mivati* of U.S. origin by serial embryo passage. Avian Diseases. 26, 305.
31. Long, P. L. and Rose, M. E. (1965). Active and passive immunization of chickens against induced infections of *Eimeria tenella*. Exp. Parasit. 16, 1.
32. Lowder, L. J. (1966). Artificial acquired immunity to *Eimeria bovis* infections in cattle. Proc. Int. Congr. Parasit. 1, 106.
33. Maniatis, T., Fritsch, E. F. and Sambrook, J. (1982). *Molecular Cloning - A Laboratory Manual*, Cold Springs Harbor Laboratory, New York.
34. Marquardt, W. C. (1980). Host and site specificity in the Coccidia; a perspective. J. Protozool. 26, 243.
35. McDonald, V. and Ballingall, S. (1982). Attenuation of *Eimeria mivati* (: *mitis*) by selection for precocious development. Parasitology 86, 371.
36. McDonald, V. and Ballingall, S. (1982). Further investigation of the pathogenicity, immunogenicity and stability of precocious *Eimeria acervulina*. Parasitology 86, 361.
37. McDonald, V., Ballingall, S. and Shirley, M. W. (1982). A preliminary study of the nature of infection and immunity in chickens given an attenuated line of *Eimeria acervulina*. Parasitology 84, 21.
38. McDougald, L. R. Status of coccidiosis: New products on way. Poult. Digest. Oct., 1981.
39. McDougald, L. R. New anticoccidial drugs: Better things to come or "endangered species?" Feedstuffs Aug. 15, 1983.
40. Millar, W. T. and Smith, J. F. B. (1983). Protein iodination using IODO-GEN™. Int J. Appl. Radiot. Isol. 34:639.
41. Miller, L. H., Mason, S. J., Dvorak, J. A., McGinniss, M. H., and Rothman, I. K. (1975) Erythrocyte receptors of (Plamodium knowlesi) Malaria: Duffy blood group determinants. Science 189, 561.
42. Reid, W. M. (1978). Protozoa. In: *Diseases of Poultry*. 7th ed. M. S. Hofstad, ed. Iowa State Univ. Press. pp. 942–1054.
43. Riley, J. F. (1980). Screening for and evaluation of anticoccidial activity. Adv. Pharm. Chemo. 17, 1.
44. Rose, M. E. (1974). Immune responses to the Eimeria: Recent observations. Sympo. Coccidia and Related Organisms. pp. 92–118. Univ. Guelph, Ontario.
45. Sanger, F. and Coulson, A. R. (1978). The use of thin polyacrylamide gels for DNA sequencing. FEBS Lett. 87, 107–110.
46. Sharma, S. D., Mullenax, J., Araujo, F. G., Erlich, H. A. and Remington, J. S. (1983). Western blot analysis of the antigens of *Toxoplasma gondii* recognized by human IgM and IgG antibodies. J. Immunology 131, 977.
47. Sharp, P. A. (1981). Speculations on RNA splicing. Cell 23, 643–646.
48. Shirley, M. W. (1980) *Eimeria necatrix*: The development and characteristics of an egg-adapted (attenuated) line. Parasitology 81, 525.
49. Shirley, M. W. (1982). Features of an attenuated line of *Eimeria praecox*. Parasitology. Proceedings of the British Soc. for Parasitology 81, 525.
50. Shirley, M. W., Bellatti, M. A. and Millard, B. J. (1982). An egg-shaped (attenuated) line of *Eimeria necatrix*: further studies on its reproduction pathogenicity and immunogenicity. Parasitology 84, 215.
51. Speer, C. A., Wong, R. B. and Schenkel, R. H. (1983). Effects of monoclonal IgG antibodies on *Eimeria tenella* (coccidia) sporozoites. J. Parasitol. 69, 775.
52. Speer, C. A., Wong, R. B. and Schenkel, R. H. (1983). Ultrastructural localization of monoclonal IgG antibodies for antigenic sites of *Eimeria tenella* oocysts, sporocysts and sporozoites. J. Protozoal. 30, 548.
53. Steiner, D. F., Quinn, P. S., Chan, S. J., Marsh, J. and Tager, H. S. (1980). Processing mechanisms in the biosynthesis of proteins. Annals N.Y. Acad. Sci. 343, 1–16.
54. Svennerholm, A., Lange, S. and Holmgrin, J. (1978). Correlation between intestinal synthesis of specific immunoglobulin A and protection against experimental cholera in mice. Inf. Imm. 21, 1.
55. Towbin, H., T. Staehelin and J. Gordon. (1979). Electrophoretic transfer of proteins from polyacrylamide gels to nitrocellulose sheets: Procedure and some applications. Proc. Nat'l. Acad. Sci. 76:4350.
56. Van Deusen, R. A. and Whetstone, C. A. (1981). Practical aspects of producing anti-viral monoclonal antibodies as diagnostic reagents. Proc. Amer. Assn. Vet. Lab. Diagnost. 24, 211.
57. Viera, J. and Messing, J. (1982). The pUC plasmids, an M13mp7-derived system for insertion mutagenesis and sequencing with synthetic universal primers. Gene 19, 259–268.
58. Wisher, M. H. (1983). Sporozoite antigens of Coccidia. J. Cellular Biochem., Supp. 7A, Abstract 0059.
59. Wong, R. B. and Schenkel, R. H. (1984). Monoclonal antibodies analysis of *Eimeria tenella* sporozoite antigens. Fed. Proc. 184, 43(6), 1630.
60. Wright, I. G., White, M., Tracey-Patte, P. D., Donaldson, R. A., Goodger, B. V., Waltisbuhl, O. J. and Mahoney, D. F. (1983). *Babesia bovis*: Isolation of a protective antigen by using monoclonal antibody. Infection and Immunity 41, 244.

What is claimed is:

1. A purified antigenic protein of *Eimeria necatrix* free of *Eimeria necatrix* sporozoites or sporocysts, which induces in a chicken an immune response conferring protection against infection of *Eimeria tenella*, the protein having a molecular weight of about 26,000 daltons and being composed of two polypeptides joined by a disulfide bond, one of the polypeptides being characterized by a molecular weight of about 18,000 daltons, by a blocked N-terminal amino acid not accessible to Edman degradation, and by the amino acid sequence set forth in FIG. 5, and the other of the polypeptides being characterized by a molecular weight of about 8,000 daltons and by the amino acid sequence set forth in FIG. 5.

* * * * *